(12) United States Patent
Yao et al.

(10) Patent No.: US 11,634,694 B2
(45) Date of Patent: Apr. 25, 2023

(54) MANGANESE PEROXIDASE, GENE THEREOF, AND USE THEREOF IN DETOXIFICATION OF MYCOTOXIN

(71) Applicant: FEED RESEARCH INSTITUTE, CHINESE ACADEMY OF AGRICULTURAL SCIENCES, Beijing (CN)

(72) Inventors: Bin Yao, Beijing (CN); Xiaoyun Su, Beijing (CN); Huang Qin, Beijing (CN); Huiying Luo, Beijing (CN); Huoqing Huang, Beijing (CN); Yingguo Bai, Beijing (CN); Yuan Wang, Beijing (CN); Yaru Wang, Beijing (CN); Rui Ma, Beijing (CN); Tao Tu, Beijing (CN); Jianshuang Ma, Beijing (CN)

( * ) Notice: Subject to any disclaimer, the term of this patent is extended or adjusted under 35 U.S.C. 154(b) by 7 days.

(21) Appl. No.: 16/618,375

(22) PCT Filed: May 31, 2017

(86) PCT No.: PCT/CN2017/086534
§ 371 (c)(1),
(2) Date: Dec. 1, 2019

(87) PCT Pub. No.: WO2018/218476
PCT Pub. Date: Dec. 6, 2018

(65) Prior Publication Data
US 2021/0139864 A1   May 13, 2021

(51) Int. Cl.
*C12N 9/02* (2006.01)
*C12N 9/08* (2006.01)
*C12N 15/63* (2006.01)

(52) U.S. Cl.
CPC ........... *C12N 9/0065* (2013.01); *C12N 15/63* (2013.01); *C12Y 111/01013* (2013.01)

(58) Field of Classification Search
CPC .................................................... C12N 9/0065
See application file for complete search history.

(56) References Cited

FOREIGN PATENT DOCUMENTS

| CN | 104232555 A | 12/2014 |
| CN | 107012131 A | 8/2017 |
| CN | 109880883   | * 6/2019 |

OTHER PUBLICATIONS

Wang. Detoxification of aflatoxin B1 by manganese peroxidase from the white-rot fungus *Phanerochaete sordida* YK-624. EMS Microbiology Letters, vol. 314, Issue 2, Jan. 2011, pp. 164-169.*
Qin. AQT03612. GenBank Database. Mar. 10, 2017.*
ISR: State Intellectual Property Office of the PR China; Feb. 26, 2018.
Wang; Jianqiao et al; "Detoxification of Aflatoxin B1 By Manganese Peroxidase From the White-Rot Fungas *Phanerochaete sordida* YK-624"; Jan. 31, 2011.
Yehia, RS "Aflatoxin Detoxification By Manganese Peroxidase Purified From Pleurotus Ostreatus", Brazilian Journal of Microbiologyl May 1, 2014.
Yu, Cun and Chi, Yujie, "AFK91528.1 Manganse Peroxidase 1"; Jun. 9, 2012.

* cited by examiner

*Primary Examiner* — Yong D Pak
(74) *Attorney, Agent, or Firm* — Patshegen IP; Moshe Pinchas

(57) ABSTRACT

The present invention provides use of a manganese peroxidase in the detoxification of mycotoxins, and specifically, the present invention provides five manganese peroxidases (MnP-1, MnP-2, MnP-4, MnP-5, and MnP-6), genes thereof, and uses thereof. The present invention provides five manganese peroxidases (MnP-1, MnP-2, MnP-4, MnP-5, and MnP-6) derived from lignocellulose degradation bacteria, the amino acid sequences thereof being as set forth in SEQ ID NO: 1, SEQ ID NO: 4, SEQ ID NO: 7, SEQ ID NO: 10, and SEQ ID NO: 13.

1 Claim, 6 Drawing Sheets

Specification includes a Sequence Listing.

SEQUENCE LISTING

```
<160> NUMBER OF SEQ ID NOS: 30

<210> SEQ ID NO 1
<211> LENGTH: 358
<212> TYPE: PRT
<213> ORGANISM: Irpex lacteus

<400> SEQUENCE: 1

Met Ala Phe Lys Thr Ile Leu Ala Phe Val Ala Leu Ala Thr Ala Ala
1               5                   10                  15

Leu Ala Ala Pro Ser Ser Arg Val Thr Cys Ser Pro Gly Arg Val Val
            20                  25                  30

Ser Asn Gly Ala Cys Cys Lys Trp Phe Asp Val Leu Asp Asp Ile Gln
        35                  40                  45

Glu Asn Leu Phe Asp Gly Gly Val Cys Gly Glu Glu Val His Glu Ser
    50                  55                  60

Leu Arg Leu Thr Phe His Asp Ala Ile Gly Phe Ser Leu Ser Ala Glu
65                  70                  75                  80

Arg Glu Gly Lys Phe Gly Gly Gly Gly Ala Asp Gly Ser Ile Met Ala
                85                  90                  95

Phe Ala Glu Ile Glu Thr Asn Phe His Ala Asn Asn Gly Val Asp Glu
            100                 105                 110

Ile Val Glu Ala Gln Arg Pro Phe Ala Ile Lys His Lys Val Ser Phe
        115                 120                 125

Gly Asp Phe Ile Gln Phe Ala Gly Ala Val Gly Val Ser Asn Cys Leu
    130                 135                 140

Gly Gly Pro Arg Leu Glu Phe Met Ala Gly Arg Ser Asn Ile Ser Arg
145                 150                 155                 160

Ala Ala Pro Asp Leu Thr Val Pro Glu Pro Ser Asp Ser Val Asp Lys
                165                 170                 175

Ile Leu Ala Arg Met Gly Asp Ala Gly Phe Ser Ser Ser Glu Val Val
            180                 185                 190

Asp Leu Leu Ile Ser His Thr Val Ala Ala Gln Asp His Val Asp Pro
        195                 200                 205

Thr Ile Pro Gly Thr Pro Phe Asp Ser Thr Pro Ser Glu Phe Asp Pro
    210                 215                 220

Gln Phe Phe Val Glu Thr Leu Leu Lys Gly Thr Leu Phe Pro Gly Asn
225                 230                 235                 240

Gly Ser Asn Val Gly Glu Leu Gln Ser Pro Leu Arg Gly Glu Phe Arg
                245                 250                 255

Leu Gln Ser Asp Ala Leu Leu Ala Arg Asp Pro Arg Thr Ala Cys Glu
            260                 265                 270

Trp Gln Ser Phe Val Asn Asn Gln Arg Leu Met Val Thr Lys Phe Glu
        275                 280                 285
```

```
Ala Val Met Ser Lys Leu Ala Val Leu Gly His Asn Pro Arg Asp Leu
        290                 295                 300
Val Asp Cys Ser Glu Val Ile Pro Val Pro Pro Arg Ala Lys Thr Asn
305                 310                 315                 320
Val Ala Val Leu Pro Ala Gly Lys Thr Arg Ala Asp Val Gln Ala Ala
                325                 330                 335
Cys Ala Ala Thr Pro Phe Pro Thr Leu Gln Thr Ala Pro Gly Pro Ala
                340                 345                 350
Thr Ser Ile Val Pro Val
            355
```

<210> SEQ ID NO 2
<211> LENGTH: 18
<212> TYPE: PRT
<213> ORGANISM: Irpex lacteus

<400> SEQUENCE: 2

```
Met Ala Phe Lys Thr Ile Leu Ala Phe Val Ala Leu Ala Thr Ala Ala
1               5                   10                  15
Leu Ala
```

<210> SEQ ID NO 3
<211> LENGTH: 340
<212> TYPE: PRT
<213> ORGANISM: Irpex lacteus

<400> SEQUENCE: 3

```
Ala Pro Ser Ser Arg Val Thr Cys Ser Pro Gly Arg Val Val Ser Asn
1               5                   10                  15
Gly Ala Cys Cys Lys Trp Phe Asp Val Leu Asp Asp Ile Gln Glu Asn
                20                  25                  30
Leu Phe Asp Gly Gly Val Cys Gly Glu Glu Val His Glu Ser Leu Arg
            35                  40                  45
Leu Thr Phe His Asp Ala Ile Gly Phe Ser Leu Ser Ala Glu Arg Glu
        50                  55                  60
Gly Lys Phe Gly Gly Gly Ala Asp Gly Ser Ile Met Ala Phe Ala
65                  70                  75                  80
Glu Ile Glu Thr Asn Phe His Ala Asn Asn Gly Val Asp Glu Ile Val
                85                  90                  95
Glu Ala Gln Arg Pro Phe Ala Ile Lys His Lys Val Ser Phe Gly Asp
                100                 105                 110
Phe Ile Gln Phe Ala Gly Ala Val Gly Val Ser Asn Cys Leu Gly Gly
            115                 120                 125
Pro Arg Leu Glu Phe Met Ala Gly Arg Ser Asn Ile Ser Arg Ala Ala
        130                 135                 140
Pro Asp Leu Thr Val Pro Glu Pro Ser Asp Ser Val Asp Lys Ile Leu
145                 150                 155                 160
Ala Arg Met Gly Asp Ala Gly Phe Ser Ser Ser Glu Val Val Asp Leu
                165                 170                 175
Leu Ile Ser His Thr Val Ala Ala Gln Asp His Val Asp Pro Thr Ile
                180                 185                 190
Pro Gly Thr Pro Phe Asp Ser Thr Pro Ser Glu Phe Asp Pro Gln Phe
            195                 200                 205
Phe Val Glu Thr Leu Leu Lys Gly Thr Leu Phe Pro Gly Asn Gly Ser
        210                 215                 220
```

-continued

Asn Val Gly Glu Leu Gln Ser Pro Leu Arg Gly Glu Phe Arg Leu Gln
225                 230                 235                 240

Ser Asp Ala Leu Leu Ala Arg Asp Pro Arg Thr Ala Cys Glu Trp Gln
                245                 250                 255

Ser Phe Val Asn Asn Gln Arg Leu Met Val Thr Lys Phe Glu Ala Val
            260                 265                 270

Met Ser Lys Leu Ala Val Leu Gly His Asn Pro Arg Asp Leu Val Asp
        275                 280                 285

Cys Ser Glu Val Ile Pro Val Pro Pro Arg Ala Lys Thr Asn Val Ala
    290                 295                 300

Val Leu Pro Ala Gly Lys Thr Arg Ala Asp Val Gln Ala Ala Cys Ala
305                 310                 315                 320

Ala Thr Pro Phe Pro Thr Leu Gln Thr Ala Pro Gly Pro Ala Thr Ser
                325                 330                 335

Ile Val Pro Val
            340

<210> SEQ ID NO 4
<211> LENGTH: 359
<212> TYPE: PRT
<213> ORGANISM: Irpex lacteus

<400> SEQUENCE: 4

Met Ala Phe Lys His Leu Val Val Ala Leu Ser Ile Val Leu Ser Leu
1               5                   10                  15

Gly Val Ala Gln Ala Ala Ile Thr Lys Arg Val Ala Cys Pro Asp Gly
            20                  25                  30

Lys Asn Thr Ala Thr Asn Ala Ala Cys Cys Ser Leu Phe Ala Ile Arg
        35                  40                  45

Asp Asp Ile Gln Ala Asn Leu Phe Asp Gly Gly Glu Cys Gly Glu Glu
    50                  55                  60

Val His Glu Ser Phe Arg Leu Thr Phe His Asp Ala Ile Gly Thr Gly
65                  70                  75                  80

Ser Phe Gly Gly Gly Gly Ala Asp Gly Ser Ile Ile Val Phe Asp Asp
                85                  90                  95

Ile Glu Thr Asn Phe His Ala Asn Asn Gly Val Asp Glu Ile Ile Asp
            100                 105                 110

Glu Gln Lys Pro Phe Ile Ala Arg His Asn Ile Thr Pro Gly Asp Phe
        115                 120                 125

Ile Gln Phe Ala Gly Ala Val Gly Val Ser Asn Cys Pro Gly Ala Pro
    130                 135                 140

Arg Leu Asp Phe Phe Leu Gly Arg Pro Asn Pro Val Ala Ala Ala Pro
145                 150                 155                 160

Asp Lys Thr Val Pro Glu Pro Phe Asp Thr Val Asp Ser Ile Leu Ala
                165                 170                 175

Arg Phe Lys Asp Ala Gly Gly Phe Thr Pro Ala Glu Ile Val Ala Leu
            180                 185                 190

Leu Gly Ser His Thr Ile Ala Ala Ala Asp His Val Asp Pro Thr Ile
        195                 200                 205

Pro Gly Thr Pro Phe Asp Ser Thr Pro Glu Val Phe Asp Thr Gln Val
    210                 215                 220

Phe Val Glu Val Gln Leu Arg Gly Thr Leu Phe Pro Gly Thr Gly Gly
225                 230                 235                 240

Asn Gln Gly Glu Val Gln Ser Pro Leu Arg Gly Glu Ile Arg Leu Gln
                245                 250                 255

```
Ser Asp His Asp Leu Ala Arg Asp Ser Arg Thr Ala Cys Glu Trp Gln
            260                 265                 270

Ser Phe Val Asn Asn Gln Ala Lys Leu Gln Ser Ala Phe Lys Ala Ala
            275                 280                 285

Phe Lys Lys Leu Ser Val Leu Gly His Asn Ile Asn Asn Leu Ile Asp
            290                 295                 300

Cys Ser Glu Val Ile Pro Glu Pro Pro Asn Val Lys Val Lys Pro Ala
305                 310                 315                 320

Thr Phe Pro Ala Gly Ile Thr His Ala Asp Val Glu Gln Ala Cys Ala
                325                 330                 335

Thr Thr Pro Phe Pro Thr Leu Ala Thr Asp Pro Gly Pro Ala Thr Ser
            340                 345                 350

Val Ala Pro Val Pro Pro Ser
            355

<210> SEQ ID NO 5
<211> LENGTH: 21
<212> TYPE: PRT
<213> ORGANISM: Irpex lacteus

<400> SEQUENCE: 5

Met Ala Phe Lys His Leu Val Val Ala Leu Ser Ile Val Leu Ser Leu
1               5                   10                  15

Gly Val Ala Gln Ala
            20

<210> SEQ ID NO 6
<211> LENGTH: 338
<212> TYPE: PRT
<213> ORGANISM: Irpex lacteus

<400> SEQUENCE: 6

Ala Ile Thr Lys Arg Val Ala Cys Pro Asp Gly Lys Asn Thr Ala Thr
1               5                   10                  15

Asn Ala Ala Cys Cys Ser Leu Phe Ala Ile Arg Asp Asp Ile Gln Ala
            20                  25                  30

Asn Leu Phe Asp Gly Gly Glu Cys Gly Glu Glu Val His Glu Ser Phe
            35                  40                  45

Arg Leu Thr Phe His Asp Ala Ile Gly Thr Gly Ser Phe Gly Gly Gly
            50                  55                  60

Gly Ala Asp Gly Ser Ile Ile Val Phe Asp Asp Ile Glu Thr Asn Phe
65                  70                  75                  80

His Ala Asn Asn Gly Val Asp Glu Ile Ile Asp Glu Gln Lys Pro Phe
            85                  90                  95

Ile Ala Arg His Asn Ile Thr Pro Gly Asp Phe Ile Gln Phe Ala Gly
            100                 105                 110

Ala Val Gly Val Ser Asn Cys Pro Gly Ala Pro Arg Leu Asp Phe Phe
            115                 120                 125

Leu Gly Arg Pro Asn Pro Val Ala Ala Pro Asp Lys Thr Val Pro
            130                 135                 140

Glu Pro Phe Asp Thr Val Asp Ser Ile Leu Ala Arg Phe Lys Asp Ala
145                 150                 155                 160

Gly Gly Phe Thr Pro Ala Glu Ile Val Ala Leu Leu Gly Ser His Thr
                165                 170                 175

Ile Ala Ala Ala Asp His Val Asp Pro Thr Ile Pro Gly Thr Pro Phe
            180                 185                 190
```

```
Asp Ser Thr Pro Glu Val Phe Asp Thr Gln Val Phe Glu Val Gln
        195                 200                 205

Leu Arg Gly Thr Leu Phe Pro Gly Thr Gly Gly Asn Gln Gly Glu Val
    210                 215                 220

Gln Ser Pro Leu Arg Gly Glu Ile Arg Leu Gln Ser Asp His Asp Leu
225                 230                 235                 240

Ala Arg Asp Ser Arg Thr Ala Cys Glu Trp Gln Ser Phe Val Asn Asn
                245                 250                 255

Gln Ala Lys Leu Gln Ser Ala Phe Lys Ala Phe Lys Lys Leu Ser
        260                 265                 270

Val Leu Gly His Asn Ile Asn Asn Leu Ile Asp Cys Ser Glu Val Ile
    275                 280                 285

Pro Glu Pro Pro Asn Val Lys Val Lys Pro Ala Thr Phe Pro Ala Gly
    290                 295                 300

Ile Thr His Ala Asp Val Glu Gln Ala Cys Ala Thr Thr Pro Phe Pro
305                 310                 315                 320

Thr Leu Ala Thr Asp Pro Gly Pro Ala Thr Ser Val Ala Pro Val Pro
                325                 330                 335

Pro Ser

<210> SEQ ID NO 7
<211> LENGTH: 366
<212> TYPE: PRT
<213> ORGANISM: Irpex lacteus

<400> SEQUENCE: 7

Met Thr Phe Lys Ala Leu Leu Ala Leu Leu Thr Val Thr Ser Ala Val
1               5                   10                  15

Leu Ala Ala Pro Gln Asp Val Thr Ala Ala Asn Lys Val Ser Cys Gly
                20                  25                  30

Gly Gly Arg Val Ala Gly His Ala Gln Cys Cys Lys Trp Tyr Asp Val
            35                  40                  45

Leu Asp Asp Ile Gln Lys Asn Leu Phe Asp Gly Gly Glu Cys Gly Glu
50                  55                  60

Glu Val His Glu Ser Leu Arg Leu Thr Phe His Asp Ala Ile Gly Phe
65                  70                  75                  80

Ser Leu Ser Ala Gln Arg Glu Gly Lys Phe Gly Gly Gly Gly Ala Asp
                85                  90                  95

Gly Ser Ile Met Ala Phe Ala Glu Ile Glu Thr Lys Phe His Ala Asn
            100                 105                 110

Asn Gly Val Asp Glu Ile Ile Glu Ala Gln Arg Pro Phe Ala Leu Asn
        115                 120                 125

His Ser Val Ser Phe Gly Asp Phe Ile Gln Phe Ala Gly Ala Val Gly
    130                 135                 140

Val Ser Asn Cys Gly Gly Gly Pro Arg Leu Gln Phe Leu Ala Gly Arg
145                 150                 155                 160

Ser Asn Ser Ser Lys Ala Ala Pro Asp Gly Thr Val Pro Glu Pro Phe
                165                 170                 175

Asp Ser Thr Asp Lys Ile Leu Ala His Met Gly Asp Ala Gly Phe Ser
            180                 185                 190

Pro Ser Glu Val Val Asp Leu Leu Ala Ser His Ser Val Ala Ala Gln
        195                 200                 205

Asp His Val Asp Ala Ser Ile Pro Gly Thr Pro Phe Asp Ser Thr Pro
    210                 215                 220
```

```
Ser Thr Phe Asp Ala Gln Phe Phe Val Glu Thr Leu Leu Lys Gly Thr
225                 230                 235                 240

Leu Phe Pro Gly Asn Gly Ser Asn Gln Gly Glu Val Gln Ser Pro Leu
            245                 250                 255

His Gly Glu Phe Arg Leu Gln Ser Asp Phe Glu Leu Ala Arg Asp Ser
        260                 265                 270

Arg Thr Ala Cys Glu Trp Gln Ser Phe Ile Thr Asp His Asn Ser Met
    275                 280                 285

Val Arg Lys Phe Glu Ala Ala Met Ala Lys Leu Ala Val Leu Gly His
290                 295                 300

Asp Pro Arg Thr Leu Ile Asp Cys Ser Asp Val Ile Pro Gln Pro Lys
305                 310                 315                 320

Gly Ala Lys Ser Asn Val Ala Val Leu Pro Ala Gly Lys His Arg Ala
            325                 330                 335

Asp Ile Gln Ala Ser Cys His Gln Thr Pro Phe Pro Thr Leu Lys Thr
        340                 345                 350

Ala Pro Gly Pro Glu Thr Ser Ile Pro Pro Val Pro Pro Ser
            355                 360                 365

<210> SEQ ID NO 8
<211> LENGTH: 18
<212> TYPE: PRT
<213> ORGANISM: Irpex lacteus

<400> SEQUENCE: 8

Met Thr Phe Lys Ala Leu Leu Ala Leu Leu Thr Val Thr Ser Ala Val
1               5                   10                  15

Leu Ala

<210> SEQ ID NO 9
<211> LENGTH: 348
<212> TYPE: PRT
<213> ORGANISM: Irpex lacteus

<400> SEQUENCE: 9

Ala Pro Gln Asp Val Thr Ala Ala Asn Lys Val Ser Cys Gly Gly Gly
1               5                   10                  15

Arg Val Ala Gly His Ala Gln Cys Cys Lys Trp Tyr Asp Val Leu Asp
            20                  25                  30

Asp Ile Gln Lys Asn Leu Phe Asp Gly Gly Glu Cys Gly Glu Glu Val
        35                  40                  45

His Glu Ser Leu Arg Leu Thr Phe His Asp Ala Ile Gly Phe Ser Leu
    50                  55                  60

Ser Ala Gln Arg Glu Gly Lys Phe Gly Gly Gly Ala Asp Gly Ser
65                  70                  75                  80

Ile Met Ala Phe Ala Glu Ile Glu Thr Lys Phe His Ala Asn Asn Gly
            85                  90                  95

Val Asp Glu Ile Ile Glu Ala Gln Arg Pro Phe Ala Leu Asn His Ser
        100                 105                 110

Val Ser Phe Gly Asp Phe Ile Gln Phe Ala Gly Ala Val Gly Val Ser
    115                 120                 125

Asn Cys Gly Gly Gly Pro Arg Leu Gln Phe Leu Ala Gly Arg Ser Asn
130                 135                 140

Ser Ser Lys Ala Ala Pro Asp Gly Thr Val Pro Glu Pro Phe Asp Ser
145                 150                 155                 160
```

Thr Asp Lys Ile Leu Ala His Met Gly Asp Ala Gly Phe Ser Pro Ser
             165                 170                 175

Glu Val Val Asp Leu Leu Ala Ser His Ser Val Ala Ala Gln Asp His
         180                 185                 190

Val Asp Ala Ser Ile Pro Gly Thr Pro Phe Asp Ser Thr Pro Ser Thr
     195                 200                 205

Phe Asp Ala Gln Phe Phe Val Glu Thr Leu Leu Lys Gly Thr Leu Phe
 210                 215                 220

Pro Gly Asn Gly Ser Asn Gln Gly Glu Val Gln Ser Pro Leu His Gly
225                 230                 235                 240

Glu Phe Arg Leu Gln Ser Asp Phe Glu Leu Ala Arg Asp Ser Arg Thr
                245                 250                 255

Ala Cys Glu Trp Gln Ser Phe Ile Thr Asp His Asn Ser Met Val Arg
            260                 265                 270

Lys Phe Glu Ala Ala Met Ala Lys Leu Ala Val Leu Gly His Asp Pro
        275                 280                 285

Arg Thr Leu Ile Asp Cys Ser Asp Val Ile Pro Gln Pro Lys Gly Ala
    290                 295                 300

Lys Ser Asn Val Ala Val Leu Pro Ala Gly Lys His Arg Ala Asp Ile
305                 310                 315                 320

Gln Ala Ser Cys His Gln Thr Pro Phe Pro Thr Leu Lys Thr Ala Pro
                325                 330                 335

Gly Pro Glu Thr Ser Ile Pro Pro Val Pro Pro Ser
            340                 345

<210> SEQ ID NO 10
<211> LENGTH: 363
<212> TYPE: PRT
<213> ORGANISM: Irpex lacteus

<400> SEQUENCE: 10

Met Ala Phe Lys Gln Leu Val Ala Thr Leu Ser Leu Ala Leu Leu Ala
1               5                   10                  15

His Gly Ala Val Val Arg Arg Val Thr Cys Pro Asp Gly Val Asn Thr
            20                  25                  30

Ala Thr Asn Ala Ala Cys Cys Ser Leu Phe Ala Val Arg Asp Asp Ile
        35                  40                  45

Gln Gln Asn Leu Phe Asp Asn Gly Gln Cys Gly Glu Asp Val His Glu
    50                  55                  60

Ser Phe Arg Leu Ser Phe His Asp Ala Ile Gly Ile Ser Pro Lys Ile
65                  70                  75                  80

Ala Ala Thr Gly Gln Phe Gly Gly Gly Ala Asp Gly Ser Ile Ile
                85                  90                  95

Leu Phe Glu Glu Ile Glu Thr Asn Phe His Ala Asn Ile Gly Val Asp
            100                 105                 110

Glu Ile Val Asp Glu Gln Lys Pro Phe Ile Ala Arg His Asn Ile Thr
        115                 120                 125

Pro Gly Asp Phe Ile Gln Phe Ala Ala Val Gly Val Ser Asn Cys
    130                 135                 140

Pro Gly Ala Pro Arg Leu Asp Phe Phe Leu Gly Arg Pro Ala Ala Thr
145                 150                 155                 160

Gln Pro Ala Pro Asp Lys Thr Val Pro Glu Pro Phe Asp Thr Val Asp
                165                 170                 175

Thr Ile Leu Glu Arg Phe Ala Asp Ala Gly Asn Phe Thr Pro Ala Glu
            180                 185                 190

```
Val Val Ala Leu Leu Val Ser His Thr Ile Ala Ala Ala Asp Glu Val
            195                 200                 205

Asp Pro Thr Ile Pro Gly Thr Pro Phe Asp Ser Thr Pro Glu Val Phe
210                 215                 220

Asp Ser Gln Phe Phe Val Glu Thr Gln Leu Arg Gly Thr Gly Phe Pro
225                 230                 235                 240

Gly Thr Ala Gly Asn Gln Gly Glu Val Glu Ser Pro Leu Ala Gly Glu
            245                 250                 255

Leu Arg Leu Gln Ser Asp Ser Glu Leu Ala Arg Asp Ser Arg Thr Ala
            260                 265                 270

Cys Glu Trp Gln Ser Phe Val Gly Asn Gln Gln Lys Ile Gln Thr Ala
            275                 280                 285

Phe Lys Ala Ala Phe Gln Lys Met Ala Val Leu Gly Val Asp Thr Ser
290                 295                 300

Lys Met Val Asp Cys Ser Glu Leu Ile Pro Val Pro Pro Glu Leu Lys
305                 310                 315                 320

Ile Thr Ala Ala His Phe Pro Ala Gly Lys Thr Asn Ala Asp Val Glu
                325                 330                 335

Gln Ala Cys Ala Ser Thr Pro Phe Pro Thr Leu Ser Thr Asp Pro Gly
                340                 345                 350

Pro Ala Thr Ser Val Ala Pro Val Pro Pro Ser
            355                 360

<210> SEQ ID NO 11
<211> LENGTH: 18
<212> TYPE: PRT
<213> ORGANISM: Irpex lacteus

<400> SEQUENCE: 11

Met Ala Phe Lys Gln Leu Val Ala Thr Leu Ser Leu Ala Leu Leu Ala
1               5                   10                  15

His Gly

<210> SEQ ID NO 12
<211> LENGTH: 345
<212> TYPE: PRT
<213> ORGANISM: Irpex lacteus

<400> SEQUENCE: 12

Ala Val Val Arg Arg Val Thr Cys Pro Asp Gly Val Asn Thr Ala Thr
1               5                   10                  15

Asn Ala Ala Cys Cys Ser Leu Phe Ala Val Arg Asp Asp Ile Gln Gln
            20                  25                  30

Asn Leu Phe Asp Asn Gly Gln Cys Gly Glu Asp Val His Glu Ser Phe
            35                  40                  45

Arg Leu Ser Phe His Asp Ala Ile Gly Ile Ser Pro Lys Ile Ala Ala
            50                  55                  60

Thr Gly Gln Phe Gly Gly Gly Gly Ala Asp Gly Ser Ile Ile Leu Phe
65                  70                  75                  80

Glu Glu Ile Glu Thr Asn Phe His Ala Asn Ile Gly Val Asp Glu Ile
                85                  90                  95

Val Asp Glu Gln Lys Pro Phe Ile Ala Arg His Asn Ile Thr Pro Gly
                100                 105                 110

Asp Phe Ile Gln Phe Ala Ala Ala Val Gly Val Ser Asn Cys Pro Gly
            115                 120                 125
```

```
Ala Pro Arg Leu Asp Phe Phe Leu Gly Arg Pro Ala Thr Gln Pro
    130                 135                 140

Ala Pro Asp Lys Thr Val Pro Glu Pro Phe Asp Thr Val Asp Thr Ile
145                 150                 155                 160

Leu Glu Arg Phe Ala Asp Ala Gly Asn Phe Thr Pro Ala Glu Val Val
                165                 170                 175

Ala Leu Leu Val Ser His Thr Ile Ala Ala Asp Glu Val Asp Pro
            180                 185                 190

Thr Ile Pro Gly Thr Pro Phe Asp Ser Thr Pro Glu Val Phe Asp Ser
        195                 200                 205

Gln Phe Phe Val Glu Thr Gln Leu Arg Gly Thr Gly Phe Pro Gly Thr
    210                 215                 220

Ala Gly Asn Gln Gly Glu Val Glu Ser Pro Leu Ala Gly Glu Leu Arg
225                 230                 235                 240

Leu Gln Ser Asp Ser Glu Leu Ala Arg Asp Ser Arg Thr Ala Cys Glu
                245                 250                 255

Trp Gln Ser Phe Val Gly Asn Gln Gln Lys Ile Gln Thr Ala Phe Lys
            260                 265                 270

Ala Ala Phe Gln Lys Met Ala Val Leu Gly Val Asp Thr Ser Lys Met
        275                 280                 285

Val Asp Cys Ser Glu Leu Ile Pro Val Pro Pro Glu Leu Lys Ile Thr
    290                 295                 300

Ala Ala His Phe Pro Ala Gly Lys Thr Asn Ala Asp Val Glu Gln Ala
305                 310                 315                 320

Cys Ala Ser Thr Pro Phe Pro Thr Leu Ser Thr Asp Pro Gly Pro Ala
                325                 330                 335

Thr Ser Val Ala Pro Val Pro Pro Ser
            340                 345

<210> SEQ ID NO 13
<211> LENGTH: 359
<212> TYPE: PRT
<213> ORGANISM: Irpex lacteus

<400> SEQUENCE: 13

Met Ala Phe Lys Gln Leu Val Ala Ala Leu Thr Val Ala Leu Ser Leu
1               5                   10                  15

Gly Val Ala Gln Gly Ala Ile Thr Arg Arg Val Ala Cys Pro Asp Gly
            20                  25                  30

Val Asn Thr Ala Thr Asn Ala Ala Cys Cys Ser Leu Phe Ala Ile Arg
        35                  40                  45

Asp Asp Ile Gln Gln Asn Leu Phe Asp Gly Gly Glu Cys Gly Glu Glu
    50                  55                  60

Val His Glu Ser Phe Arg Leu Thr Phe His Asp Ala Ile Gly Ile Gly
65                  70                  75                  80

Ser Asn Gly Gly Gly Gly Ala Asp Gly Ser Ile Ala Val Phe Glu Asp
                85                  90                  95

Ile Glu Thr Ala Phe His Ala Asn Asn Gly Val Asp Glu Ile Ile Asp
            100                 105                 110

Glu Gln Lys Pro Phe Leu Ala Arg His Asn Ile Thr Pro Gly Asp Phe
        115                 120                 125

Ile Gln Phe Ala Gly Ala Val Gly Val Ser Asn Cys Pro Gly Ala Pro
    130                 135                 140

Arg Leu Asp Phe Phe Leu Gly Arg Pro Asn Pro Val Ala Pro Ala Pro
145                 150                 155                 160
```

```
Asp Lys Thr Val Pro Glu Pro Phe Asp Thr Val Asp Ser Ile Leu Ala
            165                 170                 175

Arg Phe Ala Asp Ala Gly Gly Phe Ser Pro Ala Glu Val Val Ala Leu
            180                 185                 190

Leu Gly Ser His Thr Ile Ala Ala Asp His Val Asp Pro Thr Ile
            195                 200                 205

Pro Gly Thr Pro Phe Asp Ser Thr Pro Glu Val Phe Asp Thr Gln Val
            210                 215                 220

Phe Leu Glu Val Gln Leu Arg Gly Thr Leu Phe Pro Gly Thr Gly Gly
225                 230                 235                 240

Asn Gln Gly Glu Val Glu Ser Pro Leu Arg Gly Glu Ile Arg Leu Gln
            245                 250                 255

Ser Asp His Asp Leu Ala Arg Asp Ser Arg Thr Ala Cys Glu Trp Gln
            260                 265                 270

Ser Phe Val Asn Asn Gln Val Lys Leu Gln Thr Ala Phe Lys Ala Ala
            275                 280                 285

Phe Lys Lys Leu Ala Val Leu Gly His Asp Val Asn Asn Met Val Asp
            290                 295                 300

Cys Ser Glu Val Ile Pro Glu Pro Pro Asn Val Lys Ile Lys Ala Ala
305                 310                 315                 320

Thr Phe Pro Ala Gly Gln Thr Asn Ala Asp Val Glu Gln Ala Cys Ala
            325                 330                 335

Ser Thr Pro Phe Pro Thr Leu Ala Thr Asp Pro Gly Pro Ala Thr Ser
            340                 345                 350

Val Ala Pro Val Pro Pro Ser
            355

<210> SEQ ID NO 14
<211> LENGTH: 21
<212> TYPE: PRT
<213> ORGANISM: Irpex lacteus

<400> SEQUENCE: 14

Met Ala Phe Lys Gln Leu Val Ala Ala Leu Thr Val Ala Leu Ser Leu
1               5                   10                  15

Gly Val Ala Gln Gly
            20

<210> SEQ ID NO 15
<211> LENGTH: 338
<212> TYPE: PRT
<213> ORGANISM: Irpex lacteus

<400> SEQUENCE: 15

Ala Ile Thr Arg Arg Val Ala Cys Pro Asp Gly Val Asn Thr Ala Thr
1               5                   10                  15

Asn Ala Ala Cys Cys Ser Leu Phe Ala Ile Arg Asp Asp Ile Gln Gln
            20                  25                  30

Asn Leu Phe Asp Gly Gly Glu Cys Gly Glu Glu Val His Glu Ser Phe
            35                  40                  45

Arg Leu Thr Phe His Asp Ala Ile Gly Ile Gly Ser Asn Gly Gly Gly
            50                  55                  60

Gly Ala Asp Gly Ser Ile Ala Val Phe Glu Asp Ile Glu Thr Ala Phe
65                  70                  75                  80

His Ala Asn Asn Gly Val Asp Glu Ile Ile Asp Glu Gln Lys Pro Phe
            85                  90                  95
```

Leu Ala Arg His Asn Ile Thr Pro Gly Asp Phe Ile Gln Phe Ala Gly
            100                 105                 110

Ala Val Gly Val Ser Asn Cys Pro Gly Ala Pro Arg Leu Asp Phe Phe
            115                 120                 125

Leu Gly Arg Pro Asn Pro Val Ala Pro Ala Pro Asp Lys Thr Val Pro
        130                 135                 140

Glu Pro Phe Asp Thr Val Asp Ser Ile Leu Ala Arg Phe Ala Asp Ala
145                 150                 155                 160

Gly Gly Phe Ser Pro Ala Glu Val Val Ala Leu Gly Ser His Thr
                165                 170                 175

Ile Ala Ala Ala Asp His Val Asp Pro Thr Ile Pro Gly Thr Pro Phe
            180                 185                 190

Asp Ser Thr Pro Glu Val Phe Asp Thr Gln Val Phe Leu Glu Val Gln
            195                 200                 205

Leu Arg Gly Thr Leu Phe Pro Gly Thr Gly Asn Gln Gly Glu Val
        210                 215                 220

Glu Ser Pro Leu Arg Gly Glu Ile Arg Leu Gln Ser Asp His Asp Leu
225                 230                 235                 240

Ala Arg Asp Ser Arg Thr Ala Cys Glu Trp Gln Ser Phe Val Asn Asn
                245                 250                 255

Gln Val Lys Leu Gln Thr Ala Phe Lys Ala Ala Phe Lys Lys Leu Ala
            260                 265                 270

Val Leu Gly His Asp Val Asn Asn Met Val Asp Cys Ser Glu Val Ile
        275                 280                 285

Pro Glu Pro Pro Asn Val Lys Ile Lys Ala Ala Thr Phe Pro Ala Gly
            290                 295                 300

Gln Thr Asn Ala Asp Val Glu Gln Ala Cys Ala Ser Thr Pro Phe Pro
305                 310                 315                 320

Thr Leu Ala Thr Asp Pro Gly Pro Ala Thr Ser Val Ala Pro Val Pro
                325                 330                 335

Pro Ser

<210> SEQ ID NO 16
<211> LENGTH: 1684
<212> TYPE: DNA
<213> ORGANISM: Irpex lacteus

<400> SEQUENCE: 16
atggctttca agactatcct tgccttcgtt gctctcgcca cagctgctct tgcggcaccc        60
tcttctagag tgacatgcag tccgggacgt gttgttagca acggagctgt aagcaattct       120
cgacaccgtc ctaccaatta taacgtctaa tggccgtcgt actagtgctg caagtggttc       180
gacgttctcg acgacatcca ggagaacctg tatgtccttc ccgttgctca gtgaaccttg       240
tcgccgctga ttccatcaca ggtttgacgg cggtgtatgt ggcgaagaag ttcacgaggt       300
aagtaacgat tacagcaggt agttgatgca tactaacagt tgctctttgc agtcgcttcg       360
tgtaagtgac tctcagaatg aacgtggtga acgcatattg acatgtgcct tccattgcca       420
agctcacttt ccacgacgcg taagtgtctg ttgtcactat tcttgcttct tgtgctgatc       480
ctgtctgtat agtattggct ttagtctctc tgctgagcgc gagggcaagt ttgggttcgt       540
acttcaactt cacaatgtcc cttttttgatg attcacatcc gcctatagtg gtggaggagc       600
tgatggctct atcatggcat cgccgagatt tgagaccaac ttccgtgcgt aaacctgggc       660
ctttgttgag tgcttatatt aaactctgaa gcagatgcaa acaatggtgt cgacgaaatt       720

```
gtcgaggcgg tatgtctctt catgtgtcca tttttcgagt cacctcactg atccatcatg    780
tatagcaacg cccattcgct atcaagcaca aagtctcctt cggcgacttc atccaatttg    840
caggggcagt cggtgtgtcg aattgccttg gtggcccccg tctcgagttc atggctggtc    900
gttccaacat ctctcgcgct gctcccgacc tcactgttcc tgagccctct gactcagttg    960
acaagatctt ggcccgcatg ggcgatgctg gcttttcctc ttcggaagtt gtggaccttc   1020
tcatttccca caccgttgca gctcaagacc acgttgatcc caccatcccc gtgagccact   1080
ctggtaatca ggcatattat tgagcaatac tcatcacgac atctacaggg aacaccttt    1140 gactccaccc cctccgaatt cgatcctcag ttcttcgtag aggtaagctt tgaccacgtc   1200
atcgtcaagc gaagcgactt aagggtcttt ttacagactc tcttgaaggg cactctgttc   1260
cctggtaacg gttccaatgt cggcgaactt cagtcccccc ttagaggaga gttccgtctt   1320
caatccgacg ctctccttgc tcgtgacccc aggaccgcct gtgaatggca atctttcgtt   1380
agtgagtatc ctcttcactt tcatgtcgag actctataat tgatgcaccc gcctgtcaga   1440
caaccaacgt ctcatggtca ccaagttcga ggccgtcatg tccaagcttg ctgtcctcgg   1500
ccacaacccg cgtgatctcg tcgactgctc ggaagtcatc cccgtgcctc cacgtgccaa   1560
gaccaatgtc gcagttctcc ccgctggcaa gactcgcgct gatgtccagg ctgcttgcgc   1620
tgctacaccc ttcccaaccc tccagaccgc ccctggcccc gccacctcca tcgttcctgt   1680
gtaa                                                                1684
```

<210> SEQ ID NO 17
<211> LENGTH: 54
<212> TYPE: DNA
<213> ORGANISM: Irpex lacteus

<400> SEQUENCE: 17

```
atggctttca agactatcct tgccttcgtt gctctcgcca cagctgctct tgcg           54
```

<210> SEQ ID NO 18
<211> LENGTH: 1023
<212> TYPE: DNA
<213> ORGANISM: Irpex lacteus

<400> SEQUENCE: 18

```
gcaccctctt ctagagtgac atgcagtccg ggacgtgttg ttagcaacgg agcttgctgc     60
aagtggttcg acgttctcga cgacatccag gagaacctgt tgacggcgg tgtatgtggc    120 gaagaagttc acgagtcgct tcgtctcact ttccacgacg ctattggctt tagtctctct    180
gctgagcgcg agggcaagtt tggtggtgga ggagctgatg gctctatcat ggcattcgcc    240
gagattgaga ccaacttcca tgcaaacaat ggtgtcgacg aaattgtcga ggcgcaacgc    300
ccattcgcta tcaagcacaa agtctccttc ggcgacttca tccaatttgc aggggcagtc    360
ggtgtgtcga attgccttgg tggcccccgt ctcgagttca tggctggtcg ttccaacatc    420
tctcgcgctg ctcccgacct cactgttcct gagccctctg actcagttga caagatcttg    480
gcccgcatgg gcgatgctgg cttttcctct tcggaagttg tggaccttct catttcccac    540
accgttgcag ctcaagacca cgttgatccc accatcccc g aacacctttt gactccacc    600 ccctccgaat tcgatcctca gttcttcgta gagactctct tgaagggcac tctgttccct    660
ggtaacggtt ccaatgtcgg cgaacttcag tccccccttta gaggagagtt ccgtcttcaa    720
tccgacgctc tccttgctcg tgaccccagg accgcctgtg aatggcaatc tttcgttaac    780
```

| | |
|---|---|
| aaccaacgtc tcatggtcac caagttcgag gccgtcatgt ccaagcttgc tgtcctcggc | 840 |
| cacaacccgc gtgatctcgt cgactgctcg gaagtcatcc ccgtgcctcc acgtgccaag | 900 |
| accaatgtcg cagttctccc cgctggcaag actcgcgctg atgtccaggc tgcttgcgct | 960 |
| gctacaccct tcccaaccct ccagaccgcc cctggccccg ccacctccat cgttcctgtg | 1020 |
| taa | 1023 |

<210> SEQ ID NO 19
<211> LENGTH: 1629
<212> TYPE: DNA
<213> ORGANISM: Irpex lacteus

<400> SEQUENCE: 19

| | |
|---|---|
| atggccttca acaccctcgt cgttgcactc tctatcgttc tctcgcttgg tgtcgcacaa | 60 |
| ggtcagtagc tcatggaata atgcgcctgc taacttcgct gatgggacta tgttgcagct | 120 |
| gcaatcacca agcgtgttgc ttgtcctgac ggcaagaata cagcgacaaa cgcggcttgc | 180 |
| tgttctttgt tcgccattcg tgatgatatc caggcaaacc tcttcgacgg tggtgaatgc | 240 |
| ggtgaagaag tccacgagtc cttccgtctg tcagtacttg actcttcta acgtatcact | 300 |
| tgtgaaattc atgcatgttt tcagcacatt ccacgacgct atcggtactg gctcttcgg | 360 |
| gtgagagatc aaagctttta tattgtgtac tctacgcctg acatttgatt atagtggcgg | 420 |
| aggtgccgat ggctccatca ttgtcttcga tgatatcgag actaacttcc acgctaacaa | 480 |
| cggcgtcgac gaaattatcg acgagcagaa gccgttcatc gccaggcaca atattccccc | 540 |
| cggcgacttg tgagctgatc ttgctattct atcgcattct gaccactaat atatacactg | 600 |
| atttcagcat tcaatttgct ggcgccgtcg gcgtctccaa ctgtcctggg gctcctcgtc | 660 |
| ttgacttctt cctcggtaag actcatttca ataccgacaa tgggcccata ctgatgatac | 720 |
| gatatccagg ccgaccaaac cctgtggctg ctgcaccgga caagactgta cctgagccat | 780 |
| tcggtcagta caccaatctt catcgtatct actccaaagc tgatgtaagg gcccctagac | 840 |
| accgtggata gcatccttgc tcgtttcaag gatgctggcg gattcactcc agctgaggta | 900 |
| gttgctctcc tcggctctca cacgatcgct gcagccgatc atgtcgaccc taccatccct | 960 |
| ggtactcctt tcgattctac tcctgaggtc ttcgatatccc aggttttcgt cgaggttcaa | 1020 |
| ctccgtggca cgctcttccc agggtgagtt tcctgttta taacacatac ctgagtctga | 1080 |
| ctgcgacttg cccattagaa ctggtggcaa ccagggcgaa gttcagtctc ctctccgcgg | 1140 |
| tgagatccgt ctccaatctg accatgatgt acgtgtacga tggatatttc gttctgggtc | 1200 |
| ttactgacaa gccttaagct cgctcgtgac tctcgaaccg cctgcgagtg gcagtcgttt | 1260 |
| gtgaacaacc aggctaagct ccaatctgct ttcaaagcag ccttcaagaa gctctcagtc | 1320 |
| cttggccaca acattaacaa cttgattgac tgctctgagg tcatccctga gccaccaaat | 1380 |
| gtcaaggtta agcccgctac cttcccagct ggcattaccc acgccgatgt cgagcaagct | 1440 |
| gtacgtgctc tttctccttt gcttcctcta tactcctaat aatctgtttc actttgtagt | 1500 |
| gcgccactac tccattcccg actctcgcta ccgaccccgg cccccgcaact tctgtcgccc | 1560 |
| ctgtgtaagt tacatctttg acttcatgtt acattatatg ctcatatcgc tttcagccct | 1620 |
| ccctcgtaa | 1629 |

<210> SEQ ID NO 20
<211> LENGTH: 63
<212> TYPE: DNA
<213> ORGANISM: Irpex lacteus

```
<400> SEQUENCE: 20
atggccttca aacacctcgt cgttgcactc tctatcgttc tctcgcttgg tgtcgcacaa    60
gct                                                                  63

<210> SEQ ID NO 21
<211> LENGTH: 1017
<212> TYPE: DNA
<213> ORGANISM: Irpex lacteus

<400> SEQUENCE: 21
gcaatcacca agcgtgttgc ttgtcctgac ggcaagaata cagcgacaaa cgcggcttgc    60
tgttctttgt cgccattcg tgatgatatc caggcaaacc tcttcgacgg tggtgaatgc    120
ggtgaagaag tccacgagtc cttccgtctc acattccacg acgctatcgg tactggctct    180
ttcggtggcg gaggtgccga tggctccatc attgtcttcg atgatatcga gactaacttc    240
cacgctaaca acgcgtcga cgaaattatc gacgagcaga agccgttcat cgccaggcac    300
aatattcccc ccggcgactt cattcaattt gctggcgccg tcggcgtctc caactgtcct    360
ggggctcctc gtcttgactt cttcctcggc cgaccaaacc ctgtggctgc tgcaccggac    420
aagactgtac ctgagccatt cgacaccgtg gatagcatcc ttgctcgttt caaggatgct    480
ggcggattca ctccagctga gatagttgct ctcctcggct ctcacacgat cgctgcagcc    540
gatcatgtcg accctaccat ccctggtact cctttcgatt ctactcctga ggtcttcgat    600
acccaggttt tcgtcgaggt tcaactccgt ggcacgctct tcccaggaac tggtggcaac    660
cagggcgaag ttcagtctcc tctccgcggt gagatccgtc tccaatctga ccatgatctc    720
gctcgtgact ctcgaaccgc ctgcgagtgg cagtcgtttg tgaacaacca ggctaagctc    780
caatctgctt tcaaagcagc cttcaagaag ctctcagtcc ttggccacaa cattaacaac    840
ttgattgact gctctgaggt catccctgag ccaccaaatg tcaaggttaa gcccgctacc    900
ttcccagctg gcattaccca cgccgatgtc gagcaagctt gcgccactac tccattcccg    960
actctcgcta ccgaccccgg ccccgcaact tctgtcgccc tgtccctcc ctcgtaa     1017

<210> SEQ ID NO 22
<211> LENGTH: 1101
<212> TYPE: DNA
<213> ORGANISM: Irpex lacteus

<400> SEQUENCE: 22
atgactttca aggctcttct tgctcttttg acgttactt ctgcggtgct cgccgctccc    60
caagacgtta ctgccgctaa caaggtatca tgcggtggag gccgtgtcgc aggtcatgct    120
caatgctgca gtggtatga cgttctcgac gacatacaga agaatttgtt tgacggtgga    180
gaatgcggtg aagaagttca cgagtctttg cgactgactt ccacgacgc gatcggcttc    240 agtctttcgg cccagcgtga agggaaattc ggcggtggag gagctgacgg ctctatcatg    300
gccttcgcag agatcgagac taaatttcac gctaacaacg gtgtcgacga gatcattgaa    360
gctcaacgcc ccttcgccct caaccacagc gtgtccttcg agatttcat ccagttcgct    420 ggtgcagtcg tgtttccaa ctgtggcggc ggccctcgac tgcagttctt ggccggtcga    480
tctaacagct ccaaggccgc acctgatggc actgtccctg agccatttga ctctactgat    540
aagatcctcg ctcacatggg cgacgctggt ttctctccga gtgaagtggt cgatctcttg    600
gcatctcatt ccgtggctgc acaggaccat gtcgacgctt ctatcccggg aaccccattc    660
```

```
gattctactc ccagcacatt cgatgcccaa ttctttgtgg agactttgct gaagggcacg    720
cttttccctg gaaatggctc taaccaaggc gaagtccagt cccctcttca cggagaattc    780
cgccttcagt ccgactttga gctcgctcgt gactcccgca ctgcttgcga gtggcagtcc    840
ttcatcaccg atcacaactc gatggttcgc aagttcgaag ccgctatggc caagctagct    900
gttctcggtc acgaccccg cactttgatt gactgttccg atgtcattcc tcaacccaag     960
ggtgccaaat ctaacgtggc tgtacttccg gctggaaagc accgtgcgga tattcaagca   1020
tcttgccatc aaacgccgtt tcccaccctc aagaccgctc ccggacccga gacctcgatt   1080
cctccagtac ctccgtcgta a                                             1101
```

<210> SEQ ID NO 23
<211> LENGTH: 54
<212> TYPE: DNA
<213> ORGANISM: Irpex lacteus

<400> SEQUENCE: 23

```
atgactttca aggctcttct tgctcttttg acggttactt ctgcggtgct cgcc           54
```

<210> SEQ ID NO 24
<211> LENGTH: 1047
<212> TYPE: DNA
<213> ORGANISM: Irpex lacteus

<400> SEQUENCE: 24

```
gctccccaag acgttactgc cgctaacaag gtatcatgcg gtggaggccg tgtcgcaggt     60
catgctcaat gctgcaagtg gtatgacgtt ctcgacgaca tacagaagaa tttgtttgac    120
ggtggagaat gcggtgaaga agttcacgag tctttgcgac tgactttcca cgacgcgatc    180
ggcttcagtc tttcggccca gcgtgaaggg aaattcggcg gtggaggagc tgacggctct    240
atcatggcct tcgcagagat cgagactaaa tttcacgcta caacggtgt cgacgagatc     300 attgaagctc aacgcccctt cgccctcaac cacagcgtgt ccttcggaga tttcatccag    360
ttcgctggtg cagtcggtgt tccaactgt ggcggcggcc ctcgactgca gttcttggcc     420
ggtcgatcta cagctccaa ggccgcacct gatggcactg ccctgagcc atttgactct      480 actgataaga tcctcgctca catgggcgac gctggtttct ctccgagtga agtggtcgat    540
ctcttggcat ctcattccgt ggctgcacag gaccatgtcg acgcttctat cccgggaacc    600
ccattcgatt ctactcccag cacattcgat gcccaattct tgtggagac tttgctgaag     660 ggcacgcttt tccctggaaa tggctctaac caaggcgaag tccagtcccc tcttcacgga    720
gaattccgcc ttcagtccga ctttgagctc gctcgtgact cccgcactgc ttgcgagtgg    780
cagtccttca tcaccgatca caactcgatg gttcgcaagt cgaagccgc tatggccaag     840 ctagctgttc tcggtcacga ccccgcact ttgattgact gttccgatgt cattcctcaa     900
cccaagggtg ccaaatctaa cgtggctgta cttccggctg aaagcaccg tgcggatatt     960 caagcatctt gccatcaaac gccgtttccc accctcaaga ccgctcccgg acccgagacc   1020
tcgattcctc cagtacctcc gtcgtaa                                       1047
```

<210> SEQ ID NO 25
<211> LENGTH: 1092
<212> TYPE: DNA
<213> ORGANISM: Irpex lacteus

<400> SEQUENCE: 25

```
atggccttca acaactcgt tgctacgctc tctctcgctc tcctcgccca tggtgccgtc      60
```

-continued

```
gtcaggcgtg tcacttgtcc cgacggagtg aacacagcca ccaacgcagc ttgctgctct      120
ttgttcgccg ttcgtgacga tatccagcag aacctcttcg acaacggcca atgcggtgaa      180
gacgtccacg aatctttccg tctctccttc cacgatgcca tcggaatctc tcccaagatt      240
gcggcaaccg ccagtttgg aggtggaggc gctgacggct ctatcatcct ctttgaggag       300
attgagacca acttccacgc taacattggt gttgacgaga ttgtcgacga gcagaagccg      360
ttcatcgcca ggcacaacat cacccccgga gacttcatcc aatttgccgc cgctgttggt     420
gtctcgaact gccctggtgc tcctcgtctc gacttcttcc ttggccgtcc cgctgctact     480
caacccgctc cagacaagac tgtccccgag cccttcgaca ccgtcgacac catcctggaa    540
cgttttgcag atgcgggaaa tttcacccca gccgaggtcg tcgctctcct cgtctcccat   600
accatcgctg ctgccgatga ggtggatccc accatcccgg gaactccctt cgactctacc   660
ccggaggtct tcgactcgca gttcttcgtc gagactcagc ttcgcggaac aggattccca   720
ggaaccgcgg gtaaccaagg tgaagtcgaa tctcctcttg ctggagaact gcgtctccag   780
tccgactcag agctcgctcg tgactccaga accgcctgcg agtggcaatc cttcgtcggc   840
aaccagcaga agatccaaac cgcgttcaag gccgctttcc agaagatggc cgttctcggg  900
gtagacacca gcaagatggt cgactgctcc gagctcattc ctgttcctcc tgagctgaag  960
atcaccgccg cgcatttccc tgctggcaag accaacgctg acgtcgagca agcttgtgct 1020
tcgaccccct tccccactct gtccactgac cccggcccgg ctacttctgt cgctcctgtc 1080
cctccgtcct aa                                                        1092

<210> SEQ ID NO 26
<211> LENGTH: 54
<212> TYPE: DNA
<213> ORGANISM: Irpex lacteus

<400> SEQUENCE: 26
atggccttca aacaactcgt tgctacgctc tctctcgctc tcctcgccca tggt           54

<210> SEQ ID NO 27
<211> LENGTH: 1038
<212> TYPE: DNA
<213> ORGANISM: Irpex lacteus

<400> SEQUENCE: 27
gccgtcgtca ggcgtgtcac ttgtcccgac ggagtgaaca cagccaccaa cgcagcttgc      60
tgctctttgt tcgccgttcg tgacgatatc cagcagaacc tcttcgacaa cggccaatgc     120
ggtgaagacg tccacgaatc tttccgtctc tccttccacg atgccatcgg aatctctccc     180
aagattgcgg caaccggcca gtttggaggt ggaggcgctg acggctctat catcctcttt    240
gaggagattg agaccaactt ccacgctaac attggtgttg acgagattgt cgacgagcag    300
aagccgttca tcgccaggca acatcacc cccgagact tcatccaatt gccgccgct      360 gttggtgtct cgaactgccc tggtgctcct cgtctcgact tcttccttgg ccgtcccgct    420
gctactcaac ccgctccaga caagactgtc cccgagccct tcgacaccgt cgacaccatc    480
ctggaacgtt ttgcagatgc gggaaatttc accccagccg aggtcgtcgc tctcctcgtc    540
tcccatacca tcgctgctgc cgatgaggtg gatcccacca tcccgggaac tcccttcgac    600
tctaccccgg aggtcttcga ctcgcagttc ttcgtcgaga ctcagcttcg cggaacagga    660
ttcccaggaa ccgcgggtaa ccaaggtgaa gtcgaatctc ctcttgctgg agaactgcgt    720
```

```
ctccagtccg actcagagct cgctcgtgac tccagaaccg cctgcgagtg gcaatccttc    780
gtcggcaacc agcagaagat ccaaaccgcg ttcaaggccg cttccagaa gatggccgtt     840 ctcggggtag acaccagcaa gatggtcgac tgctccgagc tcattcctgt tcctcctgag    900
ctgaagatca ccgccgcgca tttccctgct ggcaagacca acgctgacgt cgagcaagct    960
tgtgcttcga ccccttccc cactctgtcc actgaccccg gcccggctac ttctgtcgct    1020
cctgtccctc cgtcctaa                                                 1038
```

<210> SEQ ID NO 28
<211> LENGTH: 1080
<212> TYPE: DNA
<213> ORGANISM: Irpex lacteus

<400> SEQUENCE: 28

```
atggccttca acaactcgt cgctgcactt acagtcgcgc tgtcactcgg tgttgcacaa     60
ggtgctatca ccagacgtgt tgcgtgcccc gacggcgtga acacggccac caacgcggcc   120
tgttgttctt tgttcgccat cgtgatgat atccaacaaa acctcttcga cggtggtgaa    180
tgtggggagg aggttcacga gtctttccgt ctgaccttcc atgatgccat cggcattggc   240
tcaaacggtg gcggaggtgc tgacggctcc attgctgttt tcgaggacat tgagaccgct   300
ttccacgcca acaacggtgt cgacgaaatc atcgacgagc agaagccgtt cctcgccaga   360
cacaacatca ccccggtga tttcattcaa ttcgctggtg ctgtcggtgt tccaactgt    420 cccggtgctc ctcgtctcga tttcttcctc ggccgaccaa acccggtcgc tcctgctcct   480
gacaagaccg ttcctgagcc tttcgatact gttgacagca ttctggctcg cttcgcggat   540
gctggtggat tcagcccggc tgaggttgtc gctcttcttg atcccacac gatcgctgca   600 gccgatcatg ttgaccccgac catccctggt acaccttcg actctactcc tgaggtgttc   660
gacacccagg tgttccttga agtccagctt cgtggaacgc tcttccccgg aactggtgga   720
aaccagggtg aagttgagtc tcctcttcgt ggtgaaatcc gtcttcagtc tgaccatgac   780
ctcgcccgtg actcgaggac ggcttgcgaa tggcagtcgt tcgtgaacaa tcaagtcaag   840
cttcagactg ccttcaaggc cgcttttcaag aagctcgctg tactcggcca cgatgtcaac  900
aacatggttg actgctccga agtcatcccc gagcccccga acgtcaagat caaggccgcg   960
accttccccg ctggccagac caacgccgat gttgagcagg cttgcgcctc cactcccttc  1020
cccactcttg ctactgaccc cggcccggct acctccgttg ccctgttcc cccgtcttaa  1080
```

<210> SEQ ID NO 29
<211> LENGTH: 63
<212> TYPE: DNA
<213> ORGANISM: Irpex lacteus

<400> SEQUENCE: 29

```
atggccttca acaactcgt cgctgcactt acagtcgcgc tgtcactcgg tgttgcacaa     60
ggt                                                                  63
```

<210> SEQ ID NO 30
<211> LENGTH: 1017
<212> TYPE: DNA
<213> ORGANISM: Irpex lacteus

<400> SEQUENCE: 30

```
gctatcacca gacgtgttgc gtgccccgac ggcgtgaaca cggccaccaa cgcggcctgt    60
tgttctttgt tcgccattcg tgatgatatc caacaaaacc tcttcgacgg tggtgaatgt   120
```

```
gggagggagg  ttcacgagtc  tttccgtctg  accttccatg  atgccatcgg  cattggctca    180
aacggtggcg  gaggtgctga  cggctccatt  gctgttttcg  aggacattga  gaccgctttc    240
cacgccaaca  acggtgtcga  cgaaatcatc  gacgagcaga  agccgttcct  cgccagacac    300
aacatcaccc  ccggtgattt  cattcaattc  gctggtgctg  tcggtgtctc  caactgtccc    360
ggtgctcctc  gtctcgattt  cttcctcggc  cgaccaaacc  cggtcgctcc  tgctcctgac    420
aagaccgttc  ctgagccttt  cgatactgtt  gacagcattc  tggctcgctt  cgcggatgct    480
ggtggattca  gcccggctga  ggttgtcgct  cttcttggat  cccacacgat  cgctgcagcc    540
gatcatgttg  acccgaccat  ccctggtaca  cctttcgact  ctactcctga  ggtgttcgac    600
acccaggtgt  tccttgaagt  ccagcttcgt  ggaacgctct  tccccggaac  tggtggaaac    660
cagggtgaag  ttgagtctcc  tcttcgtggt  gaaatccgtc  ttcagtctga  ccatgacctc    720
gcccgtgact  cgaggacggc  ttgcgaatgg  cagtcgttcg  tgaacaatca  agtcaagctt    780
cagactgcct  tcaaggccgc  tttcaagaag  ctcgctgtac  tcggccacga  tgtcaacaac    840
atggttgact  gctccgaagt  catccccgag  cccccgaacg  tcaagatcaa  ggccgcgacc    900
ttccccgctg  gccagaccaa  cgccgatgtt  gagcaggctt  gcgcctccac  tcccttcccc    960
actcttgcta  ctgaccccgg  cccggctacc  tccgttgccc  ctgttccccc  gtcttaa     1017
```

MANGANESE PEROXIDASE, GENE THEREOF, AND USE THEREOF IN DETOXIFICATION OF MYCOTOXIN

FIELD OF THE INVENTION

The present invention relates to the field of genetic engineering, particularly to five manganese peroxidases, i.e. MnP-1, MnP-2, MnP-4, MnP-5 and MnP-6, genes thereof, vector containing these genes, and application thereof.

BACKGROUND OF THE INVENTION

Mycotoxin is a kind of fugal secondary metabolite with the different structure and properties, which is harmful to the health of livestock, poultry and human, and is widely spread in the food and the feed contaminated by mold, thus attracting the worldwide concern on the safety of the food and the feed. The common mycotoxins include aflatoxin, zearalenone, vomitoxin (deoxynivalenol), citrinin, ochratoxin, fumaricin, patulin, and monosporotoxin, which may be classified into two types of toxins with or without a ring structure. Most of mycotoxins, such as aflatoxin and zearalenone, belong to the sub-group with the ring structure, and are usually synthesized by the fungal polyketo pathway. Aflatoxin B1, for example, is a strong liver carcinogen produced by *Aspergillus flavus*, with a core coumarin ring, two five-carbon rings on its both sides and two side-by-side dihydrofuran rings. In addition, zearalenone is a mesodihydroxybenzoate phenolide. In contrast, fumonisin has P-aminophenol linear skeleton of 22 carbons with two malonic acids side chains.

Physical adsorption (or inactivation) and bioconversion are the two main ways to detoxify mycotoxins in the food and feed. It is an increasingly popular method of detoxifying mycotoxins by using microorganisms, especially enzymes produced by microorganisms. It has been reported that laccase, pan-lylytic lactone hydrolase, peroxidase and some enzymes not yet classified can degrade aflatoxin and zearalenone by oxidation or hydrolysis mechanism. There are more and more evidences demonstrating that other enzymes with unknown properties may also be involved in the degradation of aflatoxin and zearalenone, which are two kinds of mycotoxins with cyclic structure. Manganese peroxidase (MnP) from lignocellulose-degrading bacteria is a group of enzymes involved in the oxidative degradation of lignin. It has been found that a few manganese peroxidases from *Phanerochaete sordida* and *Pleurotus ostreatus* are capable to degrade aflatoxin, but it is still not known whether other manganese peroxidases capable of degrading mycotoxins.

*Irpex lacteus* is a kind of white rot fungus, which can effectively degrade lignocellulose. Biochemical, genomic and transcriptomics analyses shows that manganese peroxidase may play an important role in the degradation of lignin. Manganese peroxidase can be used not only in degradation of lignin but also in the remediation of environmental pollution caused by synthetic dyes and polycyclic aromatic hydrocarbons. The present invention cloned and expressed five manganese peroxidase genes from *Irpex lacteus*, and analyzed their ability to degrade aflatoxin, zearalenone, and vomitoxin.

Order of the Invention

One order of the present invention is to provide five manganese peroxidases that can be efficiently applied to the detoxification of mycotoxin.

Another order of the present invention is to provide genes encoding the above manganese peroxidases.

Another order of the present invention is to provide a recombinant vector comprising the above genes.

Another order of the present invention is to provide a recombinant strain comprising the above gene.

Another order of the present invention is to provide a method of preparing the above manganese peroxidases.

Another order of the present invention is to provide application of the above manganese peroxidases to detoxify mycotoxin.

SUMMARY OF THE INVENTION

The present invention isolated five novel manganese peroxidases MnP-1, MnP-2, MnP-4, MnP-5 and MnP-6, with the amino acids sequence as shown in SEQ ID NO. 1, SEQ ID NO. 4, SEQ ID NO. 7, SEQ ID NO. 10 and SEQ ID NO. 13, respectively.

(MnP-1):
SEQ ID NO. 1
MAFKTILAFVALATAALAAPSSRVTCSPGRVVSNGACCKWFDVLDDIQEN

LFDGGVCGEEVHESLRLTFHDAIGFSLSAEREGKFGGGGADGSIMAFAEI

ETNFHANNGVDEIVEAQRPFAIKHKVSFGDFIQFAGAVGVSNCLGGPRLE

FMAGRSNISRAAPDLTVPEPSDSVDKILARMGDAGFSSSEVVDLLISHTV

AAQDHVDPTIPGTPFDSTPSEPDPQFFVETLLKGTLFPGNGSNVGELQSP

LRGEFRLQSDALLARDPRTACEWQSFVNNQRLMVTKFEAVMSKLAVLGHN

PRDLVDCSEVIPVPPRAKTNVAVLPAGKTRADVQAACAATPFPTLQTAPG

PATSIVPV

Manganese peroxidases MnP-1 includes 358 amino acids with a signal peptide of 18 amino acids, "MAFKTILAFVALATAALA", in N-terminal, as set in forth in SEQ ID NO. 2.

SEQ ID NO. 2
MAFKTILAFVALATAALA

Thereof, the mature manganese peroxidases MnP-1 protein has the amino acids as shown in SEQ ID NO. 3, and a theoretical molecular weight of 36.1 kDa.

SEQ ID NO. 3:
APSSRVTCSPGRVVSNGACCKWFDVLDDIQENLFDGGVCGEEVHESLRLT

FHDAIGFSLSAEREGKFGGGGADGSIMAFAEIETNFHANNGVDEIVEAQR

PFAIKHKVSFGDFIQFAGAVGVSNCLGGPRLEFMAGRSNISRAAPDLTVP

EPSDSVDKILARMGDAGFSSSEVVDLLISHTVAAQDHVDPTIPGTPFDST

PSEFDPQFFVETLLKGTLFPGNGSNVGELQSPLRGEFRLQSDALLARDPR

TACEWQSFVNNQRLMVTKFEAVMSKLAVLGHNPRDLVDCSEVIPVPPRAK

TNVAVLPAGKTRADVQAACAATPFPTLQTAPGPATSIVPV (MnP-2):
SEQ ID NO. 4
MAFKHLVVALSIVLSLGVAQAAITKRVACPDGKNTATNAACCSLFAIRDD

IQANLFDGGECGEEVHESFRLTFHDAIGTGSFGGGGADGSIIVFDDIETN

FHANNGVDEIIDEQKPFIARHNITPGDFIQFAGAVGVSNCPGAPRLDFFL

GRPNPVAAAPDKTVPEPFDTVDSILARFKDAGGFTPAEIVALLGSHTIAA

ADHVDPTIPGTPFDSTPEVFDTQVFVEVQLRGTLFPGTGGNQGEVQSPLR

GEIRLQSDHDLARDSRTACEWQSFVNNQAKLQSAFKAAFKKLSVLGHNIN

NLIDCSEVIPEPPNVKVKPATFPAGITHADVEQACATTPFPTLATDPGPA

TSVAPVPPS

Manganese peroxidase MnP-2 contains 359 amino acids with a signal peptide of 21 amino acids, "MAFKHLVVAL-SIVLSLGVAQA", in N-terminal, as set in forth in SEQ ID NO. 5.

Thereof, the mature manganese peroxidase MnP-2 protein has the amino acids as shown in SEQ ID NO. 6, and a theoretical molecular weight of 35.6 kDa.

SEQ ID NO. 6:
AITKRVACPDGKNTATNAACCSLFAIRDDIQANLFDGGECGEEVHESFRL

TFHDAIGTGSFGGGGADGSIIVFDDIETNFHANNGVDEIIDEQKPFIARH

NITPGDFIQFAGAVGVSNCPGAPRLDFFLGRPNPVAAAPDKTVPEPFDTV

DSILARFKDAGGFTPAEIVALLGSHTIAAADHVDPTIPGTPFDSTPEVFD

TQVFVEVQLRGTLFPGTGGNQGEVQSPLRGEIRLQSDHDLARDSRTACEW

QSFVNNQAKLQSAFKAAFKKLSVLGHNINNLIDCSEVIPEPPNVKVKPAT

FPAGITHADVEQACATTPFPTLATDPGPATSVAPVPPS (MnP-4):
SEQ ID NO. 7
MTFKALLALLTVTSAVLAAPQDVTAANKVSCGGGRVAGHAQCCKWYDVLD

DIQKNLFDGGECGEEVHESLRLTFHDAIGFSLSAQREGKFGGGGADGSIM

AFAEIETKFHANNGVDEIIEAQRPFALNHSVSFGDFIQFAGAVGVSNCGG

GPRLQFLAGRSNSSKAAPDGTVPEPFDSTDKILAHMGDAGFSPSEVVDLL

ASHSVAAQDHVDASIPGTPFDSTPSTFDAQFFVETLLKGTLFPGNGSNQG

EVQSPLHGEFRLQSDFELARDSRTACEWQSFITDHNSMVRKFEAAMAKLA

VLGHDPRTLIDCSDVIPQPKGAKSNVAVLPAGKHRADIQASCHQTPFPTL

KTAPGPETSIPPVPPS

Manganese peroxidase MnP-4 contains 365 amino acids with a signal peptide of 18 amino acids, "MTFKAL-LALLTVTSAVLA", in N-terminal, as set in forth in SEQ ID NO. 8

Thereof, the mature manganese peroxidase MnP-4 protein has the amino acids as shown in SEQ ID NO. 9, and a theoretical molecular weight of 36.8 kDa.

SEQ ID NO. 9:
APQDVTAANKVSCGGGRVAGHAQCCKWYDVLDDIQKNLFDGGECGEEVHE

SLRLTFHDAIGFSLSAQREGKFGGGGADGSIMAFAEIETKFHANNGVDEI

IEAQRPFALNHSVSFGDFIQFAGAVGVSNCGGGPRLQFLAGRSNSSKAAP

DGTVPEPFDSTDKILAHMGDAGFSPSEVVDLLASHSVAAQDHVDASIPGT

PFDSTPSTFDAQFFVETLLKGTLFPGNGSNQGEVQSPLHGEFRLQSDFEL

ARDSRTACEWQSFITDHNSMVRKFEAAMAKLAVLGHDPRTLIDCSDVIPQ

PKGAKSNVAVLPAGKHRADIQASCHQTPFPTLKTAPGPETSIPPVPPS (MnP-5):
SEQ ID NO. 10
MAFKQLVATLSLALLAHGAVVRRVTCPDGVNTATNAACCSLFAVRDDIQQ

NLFDNGQCGEDVHESFRLSFHDAIGISPKIAATGQFGGGGADGSIILFEE

IETNFHANIGVDEIVDEQKPFIARHNITPGDFIQFAAAVGVSNCPGAPRL

DFFLGRPAATQPAPDKTVPEPFDTVDTILERFADAGNFTPAEVVALLVSH

TIAAADEVDPTIPGTPFDSTPEVFDSQFFVETQLRGTGFPGTAGNQGEVE

SPLAGELRLQSDSELARDSRTACEWQSFVGNQQKIQTAFKAAFQKMAVLG

VDTSKMVDCSELIPVPPELKITAAHFPAGKTNADVEQACASTPFPTLSTD

PGPATSVAPVPPS

Manganese peroxidase MnP-5 contains 363 amino acids with a signal peptide of 18 amino acids, "MAFKQL-VATLSLALLAHG", in N-terminal, as set in forth in SEQ ID NO. 11.

Thereof, the mature manganese peroxidase MnP-5 protein has the amino acids as shown in SEQ ID NO. 12, and a theoretical molecular weight of 36.5 kDa.

SEQ ID NO. 12:
AVVRRVTCPDGVNTATNAACCSLFAVRDDIQQNLFDNGQCGEDVHESFRL

SFHDAIGISPKIAATGQFGGGGADGSIILFEEIETNFHANIGVDEIVDEQ

KPFIARHNITPGDFIQFAAAVGVSNCPGAPRLDFFLGRPAATQPAPDKTV

PEPFDTVDTILERFADAGNFTPAEVVALLVSHTIAAADEVDPTIPGTPFD

STPEVFDSQFFVETQLRGTGFPGTAGNQGEVESPLAGELRLQSDSELARD

SRTACEWQSFVGNQQKIQTAFKAAFQKMAVLGVDTSKMVDCSELIPVPPE

LKITAAHFPAGKTNADVEQACASTPFPTLSTDPGPATSVAPVPPS (MnP-6):
SEQ ID NO. 13
MAFKQLVAALTVALSLGVAQGAITRRVACPDGVNTATNAACCSLFAIRDD

IQQNLFDGGECGEEVHESFRLTFHDAIGIGSNGGGGADGSIAVFEDIETA

FHANNGVDEIIDEQKPFLARHNITPGDFIQFAGAVGVSNCPGAPRLDFFL

GRPNPVAPAPDKTVPEPFDTVDSILARFADAGGFSPAEVVALLGSHTIAA

ADHVDPTIPGTPFDSTPEVFDTQVFLEVQLRGTLFPGTGGNQGEVESPLR

GEIRLQSDHDLARDSRTACEWQSFVNNQVKLQTAFKAAFKKLAVLGHDVN

NMVDCSEVIPEPPNVKIKAATFPAGQTNADVEQACASTPFPTLATDPGPA

TSVAPVPPS

Manganese peroxidase MnP-6 contains 359 amino acids with a signal peptide of 21 amino acids, "MAFKQLVAALTVALSLGVAQG", in N-terminal, as set in forth in SEQ ID NO. 14.

Thereof, the mature manganese peroxidase MnP-6 protein has the amino acids as shown in SEQ ID NO. 15, and a theoretical molecular weight of 36.5 kDa

SEQ ID NO. 15:
AITRRVACPDGVNTATNAACCSLFAIRDDIQQNLFDGGECGEEVHESFRL

TFHDAIGIGSNGGGGADGSIAVFEDIETAFHANNGVDEIIDEQKPFLARH

NITPGDFIQFAGAVGVSNCPGAPRLDFFLGRPNPVAPAPDKTVPEPFDTV

DSILARFADAGGFSPAEVVALLGSHTIAAADHVDPTIPGTPFDSTPEVFD

-continued

TQVFLEVQLRGTLFPGTGGNQGEVESPLRGEIRLQSDHDLARDSRTACEW

QSFVNNQVKLQTAFKAAFKKLAVLGHDVNNMVDCSEVIPEPPNVKIKAAT

FPAGQTNADVEQACASTPFPTLATDPGPATSVAPVPPS

Yet another aspect of the invention is to provide the genes encoding the above manganese peroxidases MnP-1, MnP-2, MnP-4, MnP-5 and MnP-6. Particularly, the gene encoding manganese peroxidase MnP-1 has a nucleotide sequence set in forth in SEQ ID NO. 16

(MnP-1):
SEQ ID NO. 16
atggctttcaagactatccttgccttcgttgctctcgccacagctgctct tgcggcaccctcttctagagtgacatgcagtccgggacgtgttgttagca acggagctgtaagcaattctcgacaccgtcctaccaattataacgtctaa tggccgtcgtactagtgctgcaagtggttcgacgttctcgacgacatcca ggagaacctgtatgtccttcccgttgctcagtgaaccttgtcgccgctga ttccatcacaggtttgacggcggtgtatgtggcgaagaagttcacgaggt aagtaacgattacagcaggtagttgatgcatactaacagttgctctttgc agtcgcttcgtgtaagtgactctcagaatgaacgtggtgaacgcatattg acatgtgccttccattgccaagctcacmccacgacgcgtaagtgtctgtt gtcactattcttgatcttgtgctgatcctgtctgtatagtattggcttta gtctctctgctgagcgcgagggcaagtttgggttcgtacttcaacttcac aatgtccctuttgatgattcacatccgcctatagtggtggaggagctgat ggctctatcatggcattcgccgagattgagaccaacttccgtgcgtaaac ctgggcctttgttgagtgcttatattaaactctgaagcagatgcaaacaa tggtgtcgacgaaattgtcgaggcggtatgtctcttcatgtgtccatttt tcgagtcacctcactgatccatcatgtatagcaacgccattcgctatca agcacaaagtctccttcggcgacttcatccaatttgcaggggcagtcggt gtgtcgaattgccttggtggccccgtctcgagttcatggctggtcgttc caacatctctcgcgctgctcccgacctcactgttcctgagccctctgact cagttgacaagatcttggcccgcatgggcgatgctggcttttcctcttcg gaagttgtggacatctcatttcccacaccgttgcagctcaagaccacgtt gatccaccatccccgtgagccactctggtaatcaggcatattattgagc aatactcatcacgacatctacagggaacaccttgactccaccccctccg aattcgatcctcagttcttcgtagaggtaagctttgaccacgtcatcgtc aagcgaagcgacttaagggtctuttacagactctcttgaagggcactctg ttccctggtaacggttccaatgtcggcgaacttcagtcccccttagagg agagttccgtcttcaatccgacgctctccttgctcgtgaccccaggaccg cctgtgaatggcaatctttcgttagtgagtatcctcttcactttcatgtc gagactctataattgatgcaccgcctgtcagacaaccaacgtctcatgg tcaccaagttcgaggccgtcatgtccaagcttgctgtcctcggccacaac ccgcgtgatctcgtcgactgctcggaagtcatccccgtgcctccacgtgc caagaccaatgtcgcagttctccccgctggcaagactcgcgctgatgtcc aggctgcttgcgctgctacacccttcccaaccctccagaccgccctggc cccgccacctccatcgttcctgtgtaa According to an embodiment, gene encoding manganese peroxidase MnP-1 was cloned by PCR, and the analysis of its DNA sequence showed its genomic sequence had full length of 1684 bp, consisting of coding sequence of 1077 bp, and an oligonucleotide sequence encoding the signal peptide as below.

SEQ ID NO. 17:
ATGGCTTTCAAGACTATCCTTGCCTTCGTTGCTCTCGCCACAGCTGCTCT

TGCG

The cDNA sequence of the mature manganese peroxidase MnP-1 has a nucleotide sequence set in forth in SEQ ID NO. 18

SEQ ID NO. 18:
gcaccctcttctagagtgacatgcagtccgggacgtgttgttagcaacgg agcttgctgcaagtggttcgacgttctcgacgacatccaggagaacctgt ttgacggcggtgtatgtggcgaagaagttcacgagtcgcttcgtctcact ttccacgacgctattggctttagtctctctgctgagcgcgagggcaagtt tggtggtggaggagctgatggctctatcatggcattcgccgagattgaga ccaacttccatgcaaacaatggtgtcgacgaaattgtcgaggcgcaacgc ccattcgctatcaagcacaaagtctccttcggcgacttcatccaatttgc aggggcagtcggtgtgtcgaattgccttggtggccccgtctcgagttca tggctggtcgttccaacatctctcgcgctgctcccgacctcactgttcct gagccctctgactcagttgacaagatcttggcccgcatgggcgatgctgg cttttcctcttcggaagttgtggaccttctcatttcccacaccgttgcag ctcaagaccacgttgatcccaccatccccggaacaccttttgactccacc ccctccgaattcgatcctcagttcttcgtagagactctcttgaagggcac tctgttccctggtaacggttccaatgtcggcgaacttcagtccccccta gaggagagttccgtcttcaatccgacgctctccttgctcgtgaccccagg accgcctgtgaatggcaatctttcgttaacaaccaacgtctcatggtcac caagttcgaggccgtcatgtccaagcttgctgtcctcggccacaacccgc gtgatctcgtcgactgctcggaagtcatccccgtgcctccacgtgccaag accaatgtcgcagttctccccgctggcaagactcgcgctgatgtccaggc tgcttgcgctgctacacccttcccaaccctccagaccgccctggccccg ccacctccatcgttcctgtgtaa The mature manganese peroxidase MnP-1 protein has a theoretical molecular weight of 36.1 kDa and is a novel manganese peroxidase.

(MnP-2):
SEQ ID NO. 19
atggccttcaaacacctcgtcgttgcactctctatcgttctctcgcttgg tgtcgcacaaggtcagtagctcatggaataatgcgcctgctaacttcgct -continued
```
gatgggactatgttgcagctgcaatcaccaagcgtgttgcttgtcctgac ggcaagaatacagcgacaaacgcggcttgctgttctttgttcgccattcg tgatgatatccaggcaaacctcttcgacggtggtgaatgcggtgaagaag tccacgagtccttccgtctgtcagtacttggactatctaacgtatcactt gtgaaattcatgcatgttttcagcacattccacgacgctatcggtactgg ctattcgggtgagagatcaaagatttatattgtgtactctacgcctgaca tttgattatagtggcggaggtgccgatggctccatcattgtcttcgatga tatcgagactaacttccacgctaacaacggcgtcgacgaaattatcgacg agcagaagccgttcatcgccaggcacaatattaccccggcgacttgtga gctgatcttgctattctatcgcattctgaccactaatatatacactgatt tcagcattcaatttgctggcgccgtcggcgtctccaactgtcctggggct cctcgtcttgacttatcctcggtaagactcatttcaataccgacaatggg cccatactgatgatacgatatccaggccgaccaaaccctgtggctgctgc accggacaagactgtacctgagccattcggtcagtacaccaatcttcatc gtatctactccaaagctgatgtaagggcccctagacaccgtggatagcat ccttgctcgtttcaaggatgctggcggattcactccagctgaggtagttg ctctcctcggctctcacacgatcgctgcagccgatcatgtcgaccctacc atccctggtactcattcgattctactcctgaggtcttcgatacccaggtt ttcgtcgaggttcaactccgtggcacgctatcccagggtgagtttcctgt tttataacacatacctgagtctgactgcgacttgcccattagaactggtg gcaaccagggcgaagttcagtctcctctccgcggtgagatccgtctccaa tctgaccatgatgtacgtgtacgatggatatttcgttctgggtcttactg acaagccttaagctcgctcgtgactctcgaaccgcctgcgagtggcagtc gtttgtgaacaaccaggctaagctccaatctgctttcaaagcagccttca agaagctctcagtccttggccacaacattaacaacttgattgactgctct gaggtcatccctgagccaccaaatgtcaaggttaagcccgctaccttccc agctggcattacccacgccgatgtcgagcaagctgtacgtgctctuctca ttgatcctctatactcctaataatctgtttcactttgtagtgcgccacta ctccattcccgactctcgctaccgaccccggcccgcaacttctgtcgcc cctgtgtaagttacatattgacttcatgttacattatatgctcatatcgc tttcagccctccctcgtaa
```

According to an embodiment, gene encoding manganese peroxidase MnP-2 was cloned by PCR, and the analysis of its DNA sequence showed genomic sequence had full length of 11692 bp, consisting of the coding sequence of 1080 bp, and an oligonucleotide sequence as below, encoding the signal peptide.

SEQ ID NO. 20
ATGGCCTTCAAACACCTCGTCGTTGCACTCTCTATCGTTCTCTCGCTTGG
TGTCGCACAAGCT

The cDNA sequence of the mature manganese peroxidase MnP-1 has a nucleotide sequence set in forth in SEQ ID NO. 21.

```
SEQ ID NO. 21:
Gcaatcaccaagcgtgttgcttgtcctgacggcaagaatacagcgacaaa cgcggcttgctgttctttgttcgccattcgtgatgatatccaggcaaacc tcttcgacggtggtgaatgcggtgaagaagtccacgagtccttccgtctc acattccacgacgctatcggtactggctctttcggtggcggaggtgccga tggctccatcattgtcttcgatgatatcgagactaacttccacgctaaca acggcgtcgacgaaattatcgacgagcagaagccgttcatcgccaggcac aatattaccccggcgacttcattcaatttgctggcgccgtcggcgtctc caactgtcctggggctcctcgtcttgacttcttcctcggccgaccaaacc ctgtggctgctgcaccggacaagactgtacctgagccattcgacaccgtg gatagcatccttgctcgtttcaaggatgctggcggattcactccagctga gatagttgctctcctcggctctcacacgatcgctgcagccgatcatgtcg acccctaccatccctggtactcctttcgattctactcctgaggtcttcgat acccaggttttcgtcgaggttcaactccgtggcacgctcttcccaggaac tggtggcaaccagggcgaagttcagtctcctctccgcggtgagatccgtc tccaatctgaccatgatctcgctcgtgactctcgaaccgcctgcgagtgg cagtcgtttgtgaacaaccaggctaagctccaatctgctttcaaagcagc cttcaagaagctctcagtccttggccacaacattaacaacttgattgact gctctgaggtcatccctgagccaccaaatgtcaaggttaagcccgctacc ttcccagctggcattacccacgccgatgtcgagcaagcttgcgccactac tccattcccgactctcgctaccgaccccggccccgcaacttctgtcgccc ctgtccctccctcgtaa
```

The mature manganese peroxidase MnP-2 protein has a theoretical molecular weight of 35.6 kDa and is a novel manganese peroxidase.

(MnP-4):
SEQ ID NO. 22
```
ATGACTTTCAAGGCTCTTCTTGCTCTTTTGACGGTTACTTCTGCGGTGCT

CGCCGCTCCCCAAGACGTTACTGCCGCTAACAAGGTATCATGCGGTGGAG

GCCGTGTCGCAGGTCATGCTCAATGCTGCAAGTGGTATGACGTTCTCGAC

GACATACAGAAGAATTTGTTTGACGGTGGAGAATGCGGTGAAGAAGTTCA

CGAGTCTTTGCGACTGACTTTCCACGACGCGATCGGCTTCAGTCTTTCGG

CCCAGCGTGAAGGGAAATTCGGCGGTGGAGGAGCTGACGGCTCTATCATG

GCCTTCGCAGAGATCGAGACTAAATTTCACGCTAACAACGGTGTCGACGA

GATCATTGAAGCTCAACGCCCCTTCGCCCTCAACCACAGCGTGTCCTTCG

GAGATTTCATCCAGTTCGCTGGTGCAGTCGGTGTTTCCAACTGTGGCGGC

GGCCCTCGACTGCAGTTCTTGGCCGGTCGATCTAACAGCTCCAAGGCCGC

ACCTGATGGCACTGTCCCTGAGCCATTTGACTCTACTGATAAGATCCTCG

CTCACATGGGCGACGCTGGTTTCTCTCCGAGTGAAGTGGTCGATCTCTTG

GCATCTCATTCCGTGGCTGCACAGGACCATGTCGACGCTTCTATCCCGGG

AACCCCATTCGATTCTACTCCCAGCACATTCGATGCCCAATTCTTTGTGG

AGACTTTGCTGAAGGGCACGCTTTTCCCTGGAAATGGCTCTAACCAAGGC
```

-continued
GAAGTCCAGTCCCCTCTTCACGGAGAATTCCGCCTTCAGTCCGACTTTGA

GCTCGCTCGTGACTCCCGCACTGCTTGCGAGTGGCAGTCCTTCATCACCG

ATCACAACTCGATGGTTCGCAAGTTCGAAGCCGCTATGGCCAAGCTAGCT

GTTCTCGGTCACGACCCCCGCACTTTGATTGACTGTTCCGATGTCATTCC

TCAACCCAAGGGTGCCAAATCTAACGTGGCTGTACTTCCGGCTGGAAAGC

ACCGTGCGGATATTCAAGCATCTTGCCATCAAACGCCGTTTCCCACCCTC

AAGACCGCTCCCGGACCCGAGACCTCGATTCCTCCAGTACCTCCGTCGTA

A

According to an embodiment, gene encoding manganese peroxidase MnP-4 was cloned by PCR, and the analysis of its DNA sequence showed genomic sequence had full length of 1760 bp, consisting of the coding sequence of 1101 bp, and an oligonucleotide sequence as below, encoding the signal peptide.

SEQ ID NO. 23
ATGACTTTCAAGGCTCTTCTTGCTCTTTTGACGGTTACTTCTGCGGTGCT

CGCC

The cDNA sequence of the mature manganese peroxidase MnP-4 has a nucleotide sequence set in forth in SEQ ID NO. 24.

SEQ ID NO. 24:
GCTCCCCAAGACGTTACTGCCGCTAACAAGGTATCATGCGGTGGAGGCCG

TGTCGCAGGTCATGCTCAATGCTGCAAGTGGTATGACGTTCTCGACGACA

TACAGAAGAATTTGTTTGACGGTGGAGAATGCGGTGAAGAAGTTCACGAG

TCTTTGCGACTGACTTTCCACGACGCGATCGGCTTCAGTCTTTCGGCCCA

GCGTGAAGGGAAATTCGGCGGTGGAGGAGCTGACGGCTCTATCATGGCCT

TCGCAGAGATCGAGACTAAATTTCACGCTAACAACGGTGTCGACGAGATC

ATTGAAGCTCAACGCCCCTTCGCCCTCAACCACAGCGTGTCCTTCGGAGA

TTTCATCCAGTTCGCTGGTGCAGTCGGTGTTTCCAACTGTGGCGGCGGCC

CTCGACTGCAGTTCTTGGCCGGTCGATCTAACAGCTCCAAGGCCGCACCT

GATGGCACTGTCCCTGAGCCATTTGACTCTACTGATAAGATCCTCGCTCA

CATGGGCGACGCTGGTTTCTCTCCGAGTGAAGTGGTCGATCTCTTGGCAT

CTCATTCCGTGGCTGCACAGGACCATGTCGACGCTTCTATCCCGGGAACC

CCATTCGATTCTACTCCCAGCACATTCGATGCCCAATTCTTTGTGGAGAC

TTTGCTGAAGGGCACGCTTTTCCCTGGAAATGGCTCTAACCAAGGCGAAG

TCCAGTCCCTCTTCACGGAGAATTCCGCCTTCAGTCCGACTTTGAGCTC

GCTCGTGACTCCCGCACTGCTTGCGAGTGGCAGTCCTTCATCACCGATCA

CAACTCGATGGTTCGCAAGTTCGAAGCCGCTATGGCCAAGCTAGCTGTTC

TCGGTCACGACCCCCGCACTTTGATTGACTGTTCCGATGTCATTCCTCAA

CCCAAGGGTGCCAAATCTAACGTGGCTGTACTTCCGGCTGGAAAGCACCG

TGCGGATATTCAAGCATCTTGCCATCAAACGCCGTTTCCCACCCTCAAGA

CCGCTCCCGGACCCGAGACCTCGATTCCTCCAGTACCTCCGTCGTAA

The mature manganese peroxidase MnP-4 protein has a theoretical molecular weight of 36.8 kDa and is a novel manganese peroxidase.

(MnP-5):

SEQ ID NO. 25
ATGGCCTTCAAACAACTCGTTGCTACGCTCTCTCTCGCTCTCCTCGCCCA

TGGTGCCGTCGTCAGGCGTGTCACTTGTCCCGACGGAGTGAACACAGCCA

CCAACGCAGCTTGCTGCTCTTTGTTCGCCGTTCGTGACGATATCCAGCAG

AACCTCTTCGACAACGGCCAATGCGGTGAAGACGTCCACGAATCTTTCCG

TCTCTCCTTCCACGATGCCATCGGAATCTCTCCCAAGATTGCGGCAACCG

GCCAGTTTGGAGGTGGAGGCGCTGACGGCTCTATCATCCTCTTTGAGGAG

ATTGAGACCAACTTCCACGCTAACATTGGTGTTGACGAGATTGTCGACGA

GCAGAAGCCGTTCATCGCCAGGCACAACATCACCCCCGGAGACTTCATCC

AATTTGCCGCCGCTGTTGGTGTCTCGAACTGCCCTGGTGCTCCTCGTCTC

GACTTCTTCCTTGGCCGTCCCGCTGCTACTCAACCCGCTCCAGACAAGAC

TGTCCCCGAGCCCTTCGACACCGTCGACACCATCCTGGAACGTTTTGCAG

ATGCGGGAAATTTCACCCCAGCCGAGGTCGTCGCTCTCCTCGTCTCCCAT

ACCATCGCTGCTGCCGATGAGGTGGATCCCACCATCCCGGGAACTCCCTT

CGACTCTACCCCGGAGGTCTTCGACTCGCAGTTCTTCGTCGAGACTCAGC

TTCGCGGAACAGGATTCCCAGGAACCGCGGGTAACCAAGGTGAAGTCGAA

TCTCCTCTTGCTGGAGAACTGCGTCTCCAGTCCGACTCAGAGCTCGCTCG

TGACTCCAGAACCGCCTGCGAGTGGCAATCCTTCGTCGGCAACCAGCAGA

AGATCCAAACCGCGTTCAAGGCCGCTTTCCAGAAGATGGCCGTTCTCGGG

GTAGACACCAGCAAGATGGTCGACTGCTCCGAGCTCATTCCTGTTCCTCC

TGAGCTGAAGATCACCGCCGCGCATTTCCCTGCTGGCAAGACCAACGCTG

ACGTCGAGCAAGCTTGTGCTTCGACCCCCTTCCCCACTCTGTCCACTGAC

CCCGGCCCGGCTACTTCTGTCGCTCCTGTCCCTCCGTCCTAA

According to an embodiment, gene encoding manganese peroxidase MnP-5 was cloned by PCR, and the analysis of its DNA sequence showed genomic sequence had full length of 1862 bp, including encoding sequence of 1092 bp, and an oligonucleotide sequence as below, encoding the signal peptide.

SEQ ID NO. 26
ATGGCCTTCAAACAACTCGTTGCTACGCTCTCTCTCGCTCTCCTCGCCCA

TGGT

The cDNA sequence of the mature manganese peroxidase MnP-5 has a nucleotide sequence set in forth in SEQ ID NO. 27.

SEQ ID NO. 27:
GCCGTCGTCAGGCGTGTCACTTGTCCCGACGGAGTGAACACAGCCACCAA

CGCAGCTTGCTGCTCTTTGTTCGCCGTTCGTGACGATATCCAGCAGAACC

TCTTCGACAACGGCCAATGCGGTGAAGACGTCCACGAATCTTTCCGTCTC

TCCTTCCACGATGCCATCGGAATCTCTCCCAAGATTGCGGCAACCGGCCA

-continued
GTTTGGAGGTGGAGGCGCTGACGGCTCTATCATCCTCTTTGAGGAGATTG
AGACCAACTTCCACGCTAACATTGGTGTTGACGAGATTGTCGACGAGCAG
AAGCCGTTCATCGCCAGGCACAACATCACCCCCGGAGACTTCATCCAATT
TGCCGCCGCTGTTGGTGTCTCGAACTGCCCTGGTGCTCCTCGTCTCGACT
TCTTCCTTGGCCGTCCCGCTGCTACTCAACCCGCTCCAGACAAGACTGTC
CCCGAGCCCTTCGACACCGTCGACACCATCCTGGAACGTTTTGCAGATGC
GGGAAATTTCACCCCAGCCGAGGTCGTCGCTCTCCTCGTCTCCCATACCA
TCGCTGCTGCCGATGAGGTGGATCCCACCATCCCGGGAACTCCCTTCGAC
TCTACCCCGGAGGTCTTCGACTCGCAGTTCTTCGTCGAGACTCAGCTTCG
CGGAACAGGATTCCCAGGAACCGCGGGTAACCAAGGTGAAGTCGAATCTC
CTCTTGCTGGAGAACTGCGTCTCCAGTCCGACTCAGAGCTCGCTCGTGAC
TCCAGAACCGCCTGCGAGTGGCAATCCTTCGTCGGCAACCAGCAGAAGAT
CCAAACCGCGTTCAAGGCCGCTTTCCAGAAGATGGCCGTTCTCGGGGTAG
ACACCAGCAAGATGGTCGACTGCTCCGAGCTCATTCCTGTTCCTCCTGAG
CTGAAGATCACCGCCGCGCATTTCCCTGCTGGCAAGACCAACGCTGACGT
CGAGCAAGCTTGTGCTTCGACCCCCTTCCCCACTCTGTCCACTGACCCCG
GCCCGGCTACTTCTGTCGCTCCTGTCCCTCCGTCCTAA The mature manganese peroxidase MnP-5 protein has a theoretical molecular weight of 36.5 kDa and is a novel manganese peroxidase.

(MnP-6):
SEQ ID NO. 28
ATGGCCTTCAAACAACTCGTCGCTGCACTTACAGTCGCGCTGTCACTCGG
TGTTGCACAAGGTGCTATCACCAGACGTGTTGCGTGCCCCGACGGCGTGA
ACACGGCCACCAACGCGGCCTGTTGTTCTTTGTTCGCCATTCGTGATGAT
ATCCAACAAAACCTCTTCGACGGTGGTGAATGTGGGGAGGAGGTTCACGA
GTCTTTCCGTCTGACCTTCCATGATGCCATCGGCATTGGCTCAAACGGTG
GCGGAGGTGCTGACGGCTCCATTGCTGTTTTCGAGGACATTGAGACCGCT
TTCCACGCCAACAACGGTGTCGACGAAATCATCGACGAGCAGAAGCCGTT
CCTCGCCAGACACAACATCACCCCCGGTGATTTCATTCAATTCGCTGGTG
CTGTCGGTGTCTCCAACTGTCCCGGTGCTCCTCGTCTCGATTTCTTCCTC
GGCCGACCAAACCCGGTCGCTCCTGCTCCTGACAAGACCGTTCCTGAGCC
TTTCGATACTGTTGACAGCATTCTGGCTCGCTTCGCGGATGCTGGTGGAT
TCAGCCCGGCTGAGGTTGTCGCTCTTCTTGGATCCCACACGATCGCTGCA
GCCGATCATGTTGACCCGACCATCCCTGGTACACCTTTCGACTCTACTCC
TGAGGTGTTCGACACCCAGGTGTTCCTTGAAGTCCAGCTTCGTGGAACGC
TCTTCCCCGGAACTGGTGGAAACCAGGGTGAAGTTGAGTCTCCTCTTCGT
GGTGAAATCCGTCTTCAGTCTGACCATGACCTCGCCCGTGACTCGAGGAC
GGCTTGCGAATGGCAGTCGTTCGTGAACAATCAAGTCAAGCTTCAGACTG
CCTTCAAGGCCGCTTTCAAGAAGCTCGCTGTACTCGGCCACGATGTCAAC
AACATGGTTGACTGCTCCGAAGTCATCCCCGAGCCCCGAACGTCAAGAT
CAAGGCCGCGACCTTCCCCGCTGGCCAGACCAACGCCGATGTTGAGCAGG

CTTGCGCCTCCACTCCCTTCCCCACTCTTGCTACTGACCCCGGCCCGGCT
ACCTCCGTTGCCCCTGTTCCCCCGTCTTAA

According to an embodiment, gene encoding manganese peroxidase MnP-6 was cloned by PCR, and the analysis of its DNA sequence showed genomic sequence had full length of 1580 bp, including encoding sequence of 11080 bp, and an oligonucleotide sequence as below, encoding the signal peptide.

SEQ ID NO. 29
ATGGCCTTCAAACAACTCGTCGCTGCACTTACAGTCGCGCTGTCACTCGG
TGTTGCACAAGGT

The cDNA sequence of the mature manganese peroxidase MnP-6 has a nucleotide sequence set in forth in SEQ ID NO. 30

SEQ ID NO. 30:
Gctatcaccagacgtgttgcgtgccccgacggcgtgaacacggccaccaa
cgcggcctgttgttctttgttcgccattcgtgatgatatccaacaaaacc
tcttcgacggtggtgaatgtggggaggaggttcacgagtctttccgtctg
accttccatgatgccatcggcattggctcaaacggtggcggaggtgctga
cggctccattgctgttttcgaggacattgagaccgctttccacgccaaca
acggtgtcgacgaaatcatcgacgagcagaagccgttcctcgccagacac
aacatcaccccggtgatttcattcaattcgctggtgctgtcggtgtctc
caactgtcccggtgctcctcgtctcgatttcttcctcggccgaccaaacc
cggtcgctcctgctcctgacaagaccgttcctgagccttcgatactgtt
gacagcattctggctcgcttcgcggatgctggtggattcagcccggctga
ggttgtcgctcttcttggatcccacacgatcgctgcagccgatcatgttg
acccgaccatccctggtacacctttcgactctactcctgaggtgttcgac
acccaggtgttccttgaagtccagcttcgtggaacgctcttccccggaac
tggtggaaaccagggtgaagttgagtctcctcttcgtggtgaaatccgtc
ttcagtctgaccatgacctcgcccgtgactcgaggacggcttgcgaatgg
cagtcgttcgtgaacaatcaagtcaagcttcagactgccttcaaggccgc
tttcaagaagctcgctgtactcggccacgatgtcaacaacatggttgact
gctccgaagtcatccccgagccccgaacgtcaagatcaaggccgcgacc
ttccccgctggccagaccaacgccgatgttgagcaggcttgcgcctccac
tcccttccccactcttgctactgaccccggcccggctacctccgttgccc
ctgttccccgtcttaa The mature manganese peroxidase MnP-6 protein has a theoretical molecular weight of 35.6 kDa and is a novel manganese peroxidase.

In another aspect, the present invention provides a derived the manganese peroxidases by substitution, deletion and/or insertion of one or more amino acid residues to the amino acid sequence as shown in SEQ ID NO. 1, SEQ ID NO. 4, SEQ ID NO. 7, SEQ ID NO. 10 or SEQ ID NO. 13, and maintaining the ability of detoxifying mycotoxin.

In a preferred embodiment, a manganese peroxidase is such an active protein having at least about 70%, 80%, 90%, 91%, 92%, 93%, 94%, 95%, 96%, 97%, 98%, or 99% identity to the full amino acid sequence as shown in SEQ ID NO. 1, SEQ ID NO. 4, SEQ ID NO. 7, SEQ ID NO. 10 or SEQ ID NO. 13.

In another aspect, the present invention provides a derived the manganese peroxidases by substitution, deletion and/or insertion of one or more amino acid residues to the amino acid sequence as shown in SEQ ID NO. 3, SEQ ID NO. 6, SEQ ID NO. 9, SEQ ID NO. 12 or SEQ ID NO. 15, and maintaining the ability of detoxifying mycotoxin.

In a preferred embodiment, a manganese peroxidase is such an active protein having at least about 70%, 80%, 90%, 91%, 92%, 93%, 94%, 95%, 96%, 97%, 98%, or 99% identity to the full amino acid sequence as shown in SEQ ID NO. 3, SEQ ID NO. 6, SEQ ID NO. 9, SEQ ID NO. 12 or SEQ ID NO. 15, and maintaining the ability of detoxifying mycotoxin.

Yet another aspect of the invention is to provide genes encoding the above manganese peroxidases MnP-1, MnP-2, MnP-4, MnP-5 or MnP-6, selected from
(a) DNA comprising a nucleotide sequence set in forth in SEQ ID NO. 16, SEQ ID NO. 18, SEQ ID NO. 19, SEQ ID NO. 21, SEQ ID NO. 22, SEQ ID NO. 24, SEQ ID NO. 25, SEQ ID NO. 27, SEQ ID NO. 28 or SEQ ID NO. 30; or
(b) DNA having a nucleotide sequence at least about 70%, 80%, 90%, 91%, 92%, 93%, 94%, 95%, 96%, 97%, 98% or 99% homology to that shown in SEQ ID NO. 16, SEQ ID NO. 18, SEQ ID NO. 19, SEQ ID NO. 21, SEQ ID NO. 22, SEQ ID NO. 24, SEQ ID NO. 25, SEQ ID NO. 27, SEQ ID NO. 28 or SEQ ID NO. 30, and encoding the proteins with the same function as that encoded by the above DNA comprising a nucleotide sequence set in forth in SEQ ID NO. 16, SEQ ID NO. 18, SEQ ID NO. 19, SEQ ID NO. 21, SEQ ID NO. 22, SEQ ID NO. 24, SEQ ID NO. 25, SEQ ID NO. 27, SEQ ID NO. 28 or SEQ ID NO. 30, wherein, the nucleotide sequence homologous to the above sequence may be codon-optimized sequences, sequences added with cleavage sites, or other known modified sequences in the art.

In another aspect, the present invention provides the recombinant vector containing the genes encoding manganese peroxidases MnP-1, MnP-2, MnP-4, MnP-5 and MnP-6. According to an embodiment of the present invention, said recombinant vectors containing the genes encoding manganese peroxidases MnP-1, MnP-2, MnP-4, MnP-5 and MnP-6 are the vector pET28a-MnP-1, the vector pET28a-MnP-2, the vector pET28a-MnP-4, the vector pET28a-MnP-5 and the vector pET28a-MnP-6. In a preferred embodiment of the present invention, the genes encoding manganese peroxidases MnP-1, MnP-2, MnP-4, MnP-5 and MnP-6 are inserted between the sites of BamHI and Not I, BamHI and XhoI, BamHI and XhoI, EcoRI and Xho, and EcoRI and NotI of the vector pPIC9, respectively, to under the control and regulation of the promoter T7 to obtain the recombinant expression vectors pET28a-MnP-1, pET28a-MnP-2, pET28a-MnP-4, pET28a-MnP-5 and pET28a-MnP-6.

The present invention provides recombinant strains comprising the above the genes encoding manganese peroxidases MnP-1, MnP-2, MnP-4, MnP-5 and MnP-6. According to the embodiment of the present invention, said recombinant strains are the *Escherichia coli* strain BL21 (DE3)/MnP-1, BL21(DE3)/MnP-2, BL21(DE3)/MnP-4, BL21(DE3)/MnP-5 and BL21(DE3)/MnP-6.

Accordingly, the invention further provides method for producing manganese peroxidase MnP-1, MnP-2, MnP-4, MnP-5 or MnP-6. In one embodiment, the method comprises steps of transforming the host cell with the above recombinant vectors to obtain the recombinant strains, culturing the recombinant strains to induce expression of recombinant manganese peroxidase, and refolding and isolating the protein.

In a preferred embodiment of the present invention, the method includes the step of transforming the *E coli* cells with the recombinant *E coli* expression plasmids to obtain the recombinant strains.

In a preferred embodiment of the present invention, the method of the present invention incudes step of transforming the *E coli* cells BL21(DE3) with the recombinant *E coli* expression plasmids to obtain recombinant *E coli* BL21 (DE3)/MnP-1, BL21(DE3)/MnP-2, BL21(DE3)/MnP-4, BL21(DE3)/MnP-5 and BL21(DE3)/MnP-6.

In another aspect, the present invention provides the application of the above manganese peroxidase MnP-1, MnP-2, MnP-4, MnP-5 or MnP-6 to detoxify mycotoxin.

BRIEF DESCRIPTIONS OF THE DRAWINGS

EMBODIMENT

Figure 1:
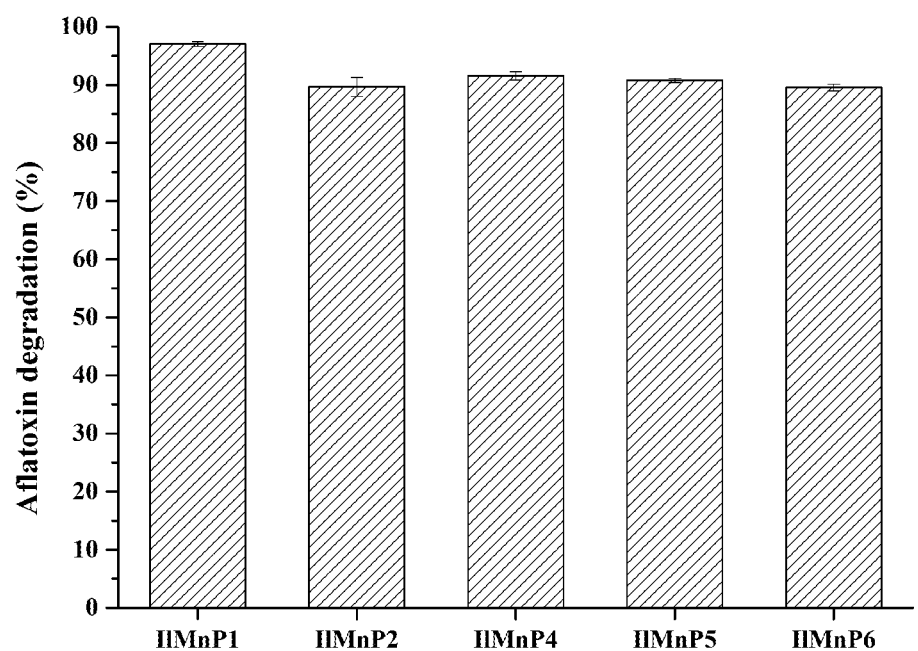
FIG. 1 shows degradation rates of aflatoxin by recombinant manganese peroxidases MnP-1, MnP-2, MnP-4, MnP-5 and MnP-6.
Figure 2:
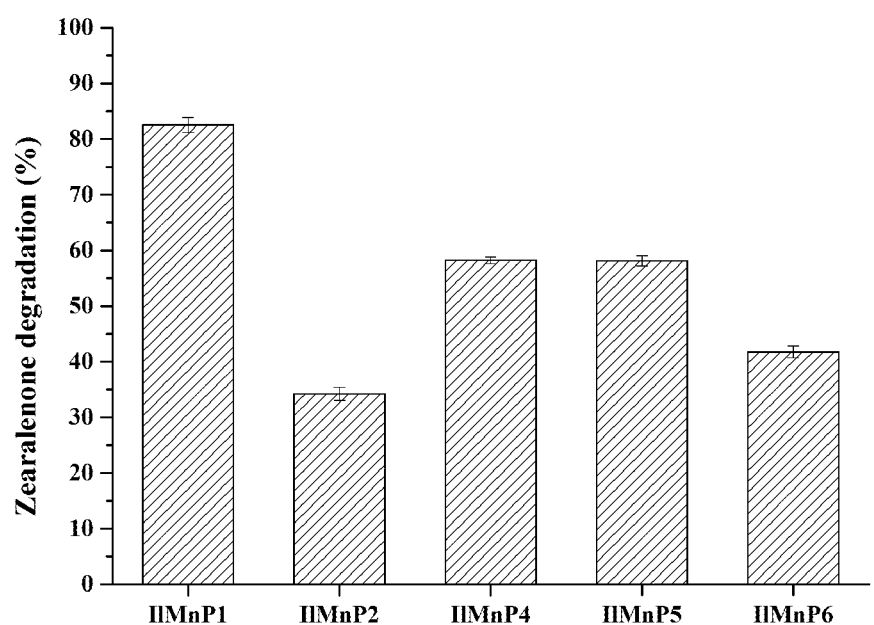
FIG. 2 shows degradation rates of zearalenone by recombinant manganese peroxidases MnP-1, MnP-2, MnP-4, MnP-5 and MnP-6.
Figure 3:
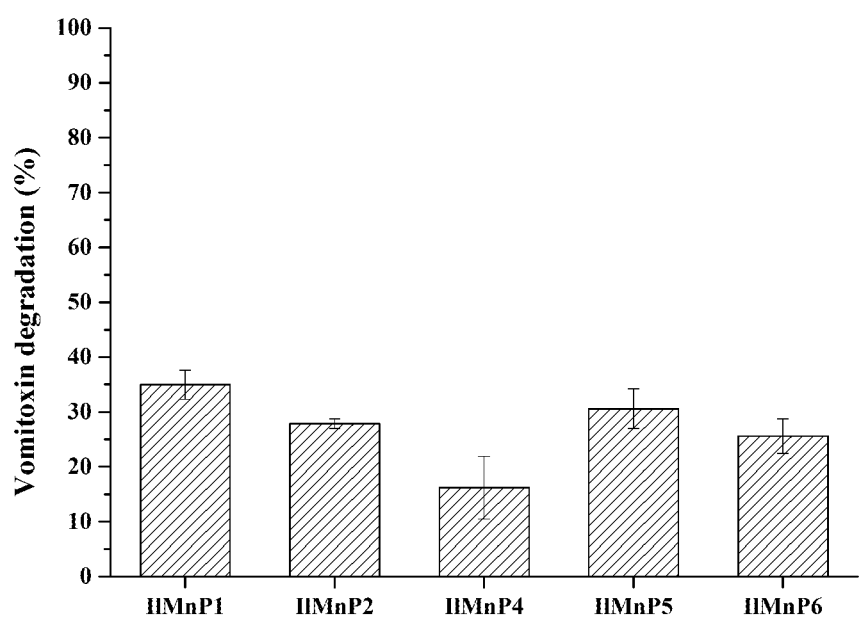
FIG. 3 shows degradation rates of vomitoxin by recombinant manganese peroxidases MnP-1, MnP-2, MnP-4, MnP-5 and MnP-6.
Figure 4:
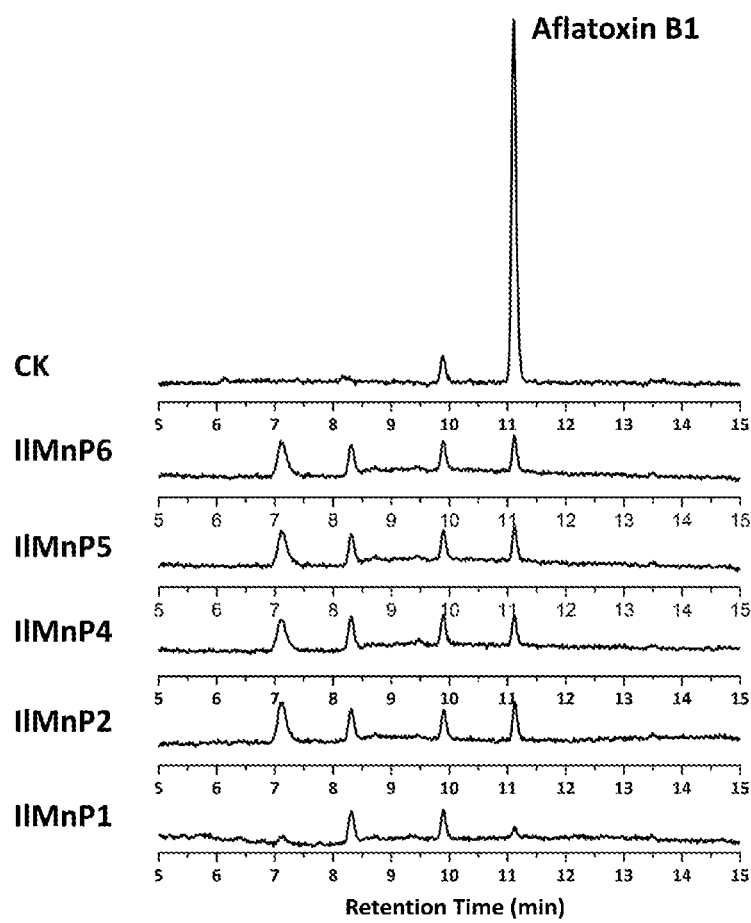
FIG. 4 shows HPLC analysis results of the degradation of aflatoxin by recombinant manganese peroxidases MnP-1, MnP-2, MnP-4, MnP-5 and MnP-6
Figure 5:
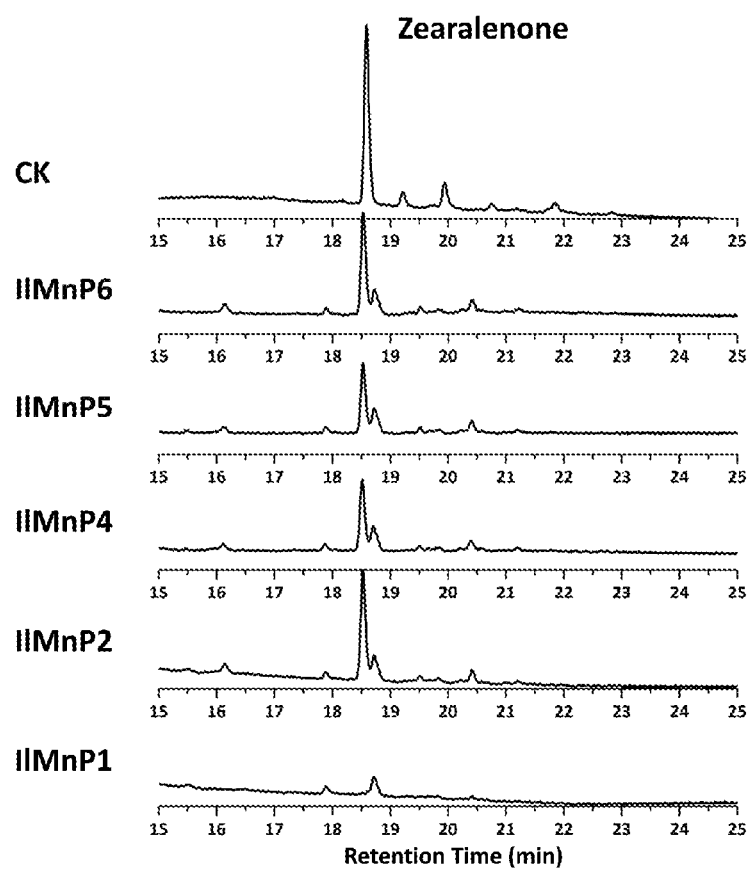
FIG. 5 shows HPLC analysis results of the degradation of zearalenone by recombinant manganese peroxidases MnP-1, MnP-2, MnP-4, MnP-5 and MnP-6.
Figure 6:
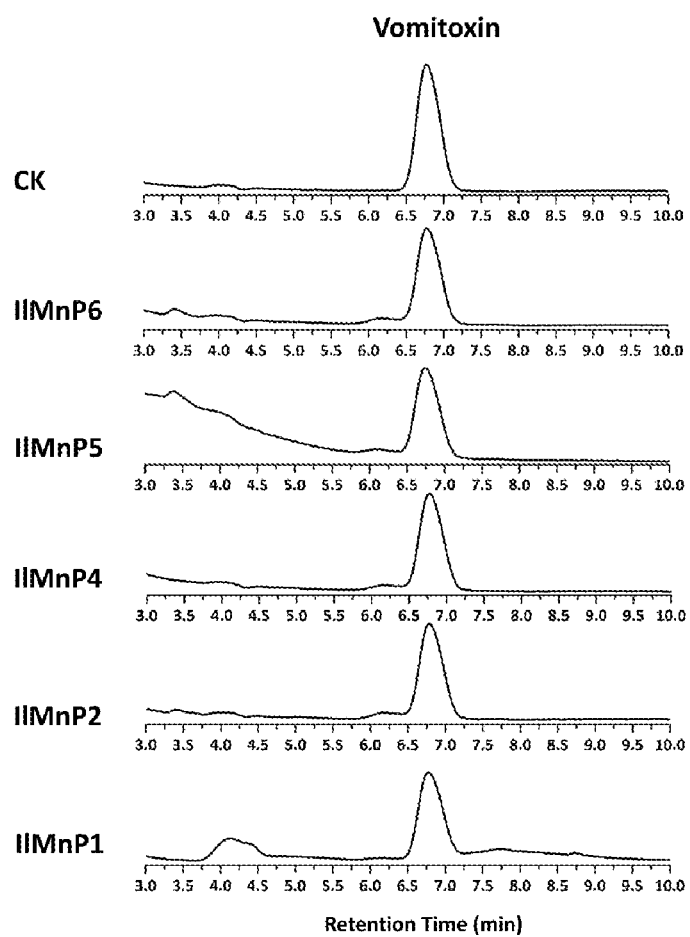
FIG. 6 shows HPLC analysis results of the degradation of vomitoxin by recombinant manganese peroxidases MnP-1, MnP-2, MnP-4, MnP-5 and MnP-6.

The present invention is further illustrated with reference to the following Examples and the appended drawings, which should by no means be construed as limitations of the present invention.

Test Materials and Reagents

1. Strains and vectors: *Irpex lacteus* from which the five genes encoding manganese peroxidases MnP-1, MnP-2, MnP-4, MnP-5 and MnP-6 were cloned respectively, the *E coli* expression vectors pET-28a(+) and strain BL21(DE3) purchased from Invitrogen.

2. Enzymes and other biochemical reagents: restriction endonucleases (Fermentas), ligase (Invitrogen), aflatoxin (Aladdin), zearalenone and vomitoxin (Sigma-Aldrich), the other reagents available purchased.

3. Medium:

(1) *Irpex lacteus* producing enzyme medium: 1% of lignocellulose, 0.2 g/L of ammonium tartrate, 2 g/L of $KH_2PO_4$, 0.71 g/L of $MgSO_4 7H_2O$, 0.1 g/L of $CaC_2$, 70 mL of macroelements concentrate.

(2) Microelement solution: 1 g/L of NaCl, 0.184 g/L of $CoCl_2.6H_2O$, 0.1 g/L of $FeSO_4.7H_2O$, 0.1 g/L of $ZnSO_4.7H_2O$, 0.1 g/L of $CuSO_4$, 0.01 g/L of $H_3BO_3$, 0.01 g/L of $Na_2MoO_4.2H_2O$, 0.01 g/L of $KAl(SO_4)_2.12H_2O$, 1.5 g/L of nitrilotriacetic acid.

(3)*E. coli*. LB medium: 1% of peptone, 0.5% of yeast extract, and 1% of NaCl, natural pH.

Suitable biology laboratory methods not particularly mentioned in the examples as below can be found in Sambrook, et al. (*Molecular Cloning: A Laboratory Manual. 2nd, ed., Cold Spring Harbor Laboratory*, Cold Spring Harbor Laboratory Press, Cold Spring Harbor, N.Y., 1989), and other kit laboratory manuals.

Example 1 Cloning Gene Encoding Manganese Peroxidase MnP-1, MnP-2, MnP-4, MnP-5 and MnP-6 from *Irpex lactus*

Isolating the total RNA of *Irpex lactus*

First, bacteria cells cultured in enzyme-producing medium for 3 days were collected on the filter paper and pressed dry, followed by adding liquid nitrogen to a high-temperature sterilized mortar and quickly ground the bacteria into powder. Then, the grounded powder was transferred to a centrifuge tube with 800 μL of Trizol, blended well and left in the room temperature for 5 min. 200 L of chloroform was added, shaken violently for 15 s, placed at room temperature for 3 min, and centrifuged at 4° C. at 12,000 RPM for 15 min. The supernatant was obtained, and isopropanol of the equal volume was added to be mixed well, placed at room temperature for 10 min and centrifuged at 4° C. at 12,000 RPM for 10 min. The supernatant was removed and the precipitation was washed twice with 70% of ethanol followed by drying in the air for 5 min, and an appropriate amount of DNase/Rnase-free deionized water was added to dissolve RNA.

The specific primers for manganese peroxidase gene were synthesized as below.

```
MnP-1:
P1:5'-CGCGGATCCGCACCCTCTTCTAGAGTGACATGCAGT-3';

P2:5'-TAAAGCGGCCGCTTACACAGGAACGATGGAGGTGGCG-3'.

MnP-2:
P3:5'-CGCGGATCCGCAATCACCAAGCGTGTTGCTTGTCCT-3';

P4:5'-CCGCTCGAGTTACGAGGGAGGGACAGGGGCGACAGA-3'.

MnP-4:
P5:5'-CGCGGATCCGCTCCCCAAGACGTTACTGCCGC-3';

P6:5'-CCGCTCGAGTTACGACGGAGGTACTGGAGGAATCG-3'.

MnP-5:
P7:5'-CGGAATTCGCCGTCGTCAGGCGTGTCACTTG-3';

P8:5'-CCGCTCGAGTTAGGACGGAGGGACAGGAGCGAC-3'.

MnP-6:
P9:5'-CGGAATTCGCTATCACCAGACGTGTTGCGTGC-3';

P10:5'-ATTTGCGGCCGCTTAAGACGGGGGAACAGGGGCAAC-3'.
```

PCR amplification was performed with cDNA obtained by RT-PCR using the total RNA of *Irpex lacteu*. PCR reaction parameters were denaturation at 95° C. for 5 min, followed by 35 cycles of denaturing at 94° C. for 30 sec, annealing at 55° C. for 30 sec, and extending at 72° C. for 1 min, and being kept at 72° C. for 10 min. After electrophoresis on 1% of agarose gel, the target fragment was cut, recovered and connected with vector pEASY-T3 for sequencing.

Example 2 Preparing the Recombinant Manganese Peroxidases

The expression vectors pET28a-MnP-1, pET28a-MnP-2, pET28a-MnP-4, pET28a-MnP-5 and pET28a-MnP-6 were constructed by connecting the gene encoding the mature manganese peroxidases MnP-1,MnP-2,MnP-4,MnP-5 and MnP-6 with the expression vector ET-28a(+), both of which were digested with restriction enzymes, and were transformed to *E coli* strain BL21(DE3) to obtain the recombinant strains BL21(DE3)/MnP-1, BL21(DE3)/MnP-2, BL21 (DE3)/MnP-4, BL21(DE3)/MnP-5 and BL21(DE3)/MnP-6.

The strain D3 containing the recombinant plasmid was planted into 40 mL of LB culture medium for culturing at 37° C. for 12 h, followed by being planted into 300 mL of LB culture medium at a ratio of 2% for culturing for 4 h at 37° C. with 250 rpm, with addition of inducer IPTG in the final concentration of 1 mM to induce for 4 h when reaching to 0.8 of $OD_{600}$, and collecting bacteria by centrifuging. The bacteria cells were lysed by Lysozyme using 8M of urea to dissolve inclusion body protein, and the refolding system prepared with 50 mM of Tris-HCl buffer with 9.5 of pH, 0.5 m M of urea, 0.5 mM of GSSG, 0.1 mM of DTT, 10 μM of hemin, 5 mM of $CaC_2$, and 0.1 mg/mL of protein solution, for renaturing for 10 h at 15° C. After the renaturated manganese peroxidase was purified, the content of protein reached to more than 95% of the total protein.

Example 3 Degradation of Aflatoxin by the Recombinant Manganese Peroxidase

Aflatoxin was dissolved into 50 mg/L of mother liquor of dimethyl sulfoxide to react for 10 h at 30° C. in the reaction system of 70 μl of malonic acid buffer (0.2 m, pH 5.0), 20 μl of aflatoxin solution, 5 μl of manganese sulfate (40 mM), 100 μl of manganese peroxidase (1000 U/L), 5 μl of hydrogen peroxide (4 mM), taking the system without manganese peroxidase as control, wherein each manganese peroxidase was set three repeats. The reaction was terminated by adding DMSO in three times of volume, to measure the degradation rate of aflatoxin in wavelength of 365 nm by high performance liquid chromatography (HPLC) using Nexera UHPLC system of which the chromatographic column is Zorbax sb-c18 (4.6×250.5 um), the mobile phase A was 0.06% of TFA water, and the mobile phase B was 0.05% TFA acetonitrile, and eluted with gradient content of 30% of solution B for 4 min, 30%-100% of solution B for 15 min, and 100% of solution B for 5 min.

Example 4 Degradation of Zearalenone by the Recombinant Manganese Peroxidase Zearalenone was dissolved into 50 mg/L of mother liquor of dimethyl sulfoxide to react for 10 h at 30° C. in the reaction system of 70 μl of malonic acid buffer (0.2 m, pH 5.0), 20 μl of aflatoxin solution, 5 μl of manganese sulfate (40 mM), 100 μl of manganese peroxidase (1000 U/L), 5 μl of hydrogen peroxide (4 mM), taking the system without manganese peroxidase as control, wherein each manganese peroxidase was set three repeats. The reaction was terminated by adding DMSO in three times of volume, to measure the degradation rate of zearalenone in wavelength of 365 nm by high performance liquid chromatography (HPLC) using Nexera UHPLC system of which the chromatographic column is Zorbax sb-c18 (4.6×250.5 um), the mobile phase A was 0.06% of TFA water, and the mobile phase B was 0.05% TFA acetonitrile, and eluted with gradient content of 30% of solution B for 4 min, 30%-100% of solution B for 15 min, and 100% of solution B for 5 min.

Example 5 Degradation of v by the Recombinant Manganese Peroxidase

Vomitoxin was dissolved into 50 mg/L of mother liquor of dimethyl sulfoxide to react for 10 h at 30° C. in the reaction system of 70 μl of malonic acid buffer (0.2 m, pH 5.0), 20 μl of aflatoxin solution, 5 μl of manganese sulfate (40 mM), 100 μl of manganese peroxidase (1000 U/L), 5 µl of hydrogen peroxide (4 mM), taking the system without manganese peroxidase as control, wherein each manganese peroxidase was set three repeats. The reaction was terminated by adding DMSO in three times of volume, to measure the degradation rate of vomitoxin in wavelength of 365 nm by high performance liquid chromatography (HPLC) using Nexera UHPLC system of which the chromatographic column is Zorbax sb-c18 (4.6×250.5 um), the mobile phase A was 0.06% of TFA water, and the mobile phase B was 0.05% TFA acetonitrile, and eluted with gradient content of 30% of solution B for 4 min, 30%-100% of solution B for 15 min, and 100% of solution B for 5 min.

The invention claimed is:

1. A method for detoxifying mycotoxin, comprising contacting said mycotoxin with manganese peroxidase, thereby degrading said mycotoxin, wherein said manganese peroxidase is a polypeptide of the amino acid sequence of SEQ ID NO:7, and said mycotoxin is zearalenone or vomitoxin.

* * * * *